(12) United States Patent
Girardin et al.

(10) Patent No.: US 8,591,499 B2
(45) Date of Patent: Nov. 26, 2013

(54) TOOLS AND METHODS FOR PROGRAMMING AN IMPLANTABLE VALVE

(75) Inventors: Yves Girardin, Le Locle (CH); Fabien Luginbühl, Le Locle (CH); Pascal Resin, Le Locle (CH); Thierry Pipoz, Le Locle (CH)

(73) Assignee: Medos International S.A.R.L. (CH)

( * ) Notice: Subject to any disclaimer, the term of this patent is extended or adjusted under 35 U.S.C. 154(b) by 766 days.

(21) Appl. No.: 12/609,715

(22) Filed: Oct. 30, 2009

(65) Prior Publication Data

US 2011/0105993 A1    May 5, 2011

(51) Int. Cl.
*A61M 5/00* (2006.01)
*A61K 9/22* (2006.01)

(52) U.S. Cl.
USPC .............................. 604/891.1; 604/9; 137/524

(58) Field of Classification Search
USPC ........ 604/891.1, 9; 128/899; 137/1, 524, 530, 137/551, 554; 251/65; 116/204, 267; 33/319, 352, 355 R, 364
See application file for complete search history.

(56) References Cited

U.S. PATENT DOCUMENTS

| | | | |
|---|---|---|---|
| 4,156,422 A * | 5/1979 | Hildebrandt et al. | ............. 604/9 |
| 4,443,214 A | 4/1984 | Marion | |
| 4,615,691 A * | 10/1986 | Hakim et al. | ..................... 604/9 |
| 4,676,772 A | 6/1987 | Hooven | |
| 5,643,194 A | 7/1997 | Negre | |
| 6,391,019 B1 * | 5/2002 | Ito | ............................. 604/891.1 |
| 7,921,571 B2 | 4/2011 | Moureaux | |
| 2005/0092335 A1 | 5/2005 | Bertrand | |
| 2005/0279960 A1 | 12/2005 | Cabaud | |
| 2007/0093714 A1 | 4/2007 | Beaucoup | |
| 2010/0249690 A1 | 9/2010 | Soares et al. | |

FOREIGN PATENT DOCUMENTS

| | | |
|---|---|---|
| EP | 136054 A2 | 4/1985 |
| EP | 1092450 A1 | 4/2001 |
| FR | 2354103 A1 | 1/1978 |
| WO | WO 0054826 A1 | 9/2000 |
| WO | 2005092424 A1 | 10/2005 |
| WO | WO 2009034410 A1 | 3/2009 |

* cited by examiner

*Primary Examiner* — Eric Keasel

(57) ABSTRACT

Integrated tools for noninvasively reading and adjusting an implantable, magnetically adjustable valve, and methods of use are disclosed. The tools include magnetic or electronic reading of the valve, and magnetic or electromagnetic adjustment of the valve. In use, the tools are positioned above or in contact with the patient's skin, in proximity to the valve.

10 Claims, 11 Drawing Sheets

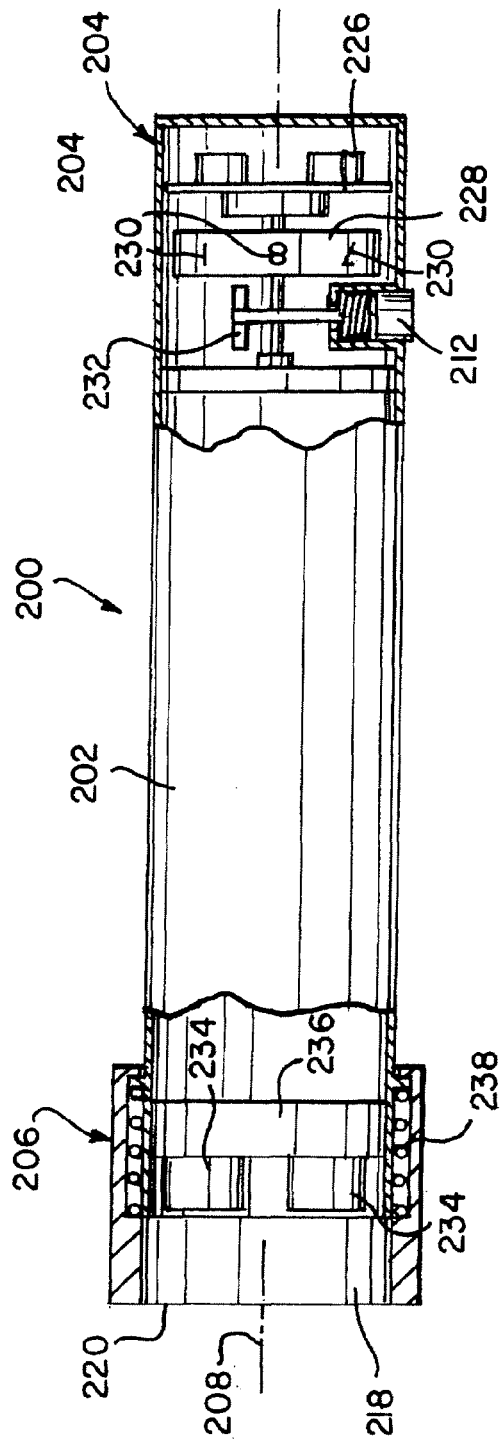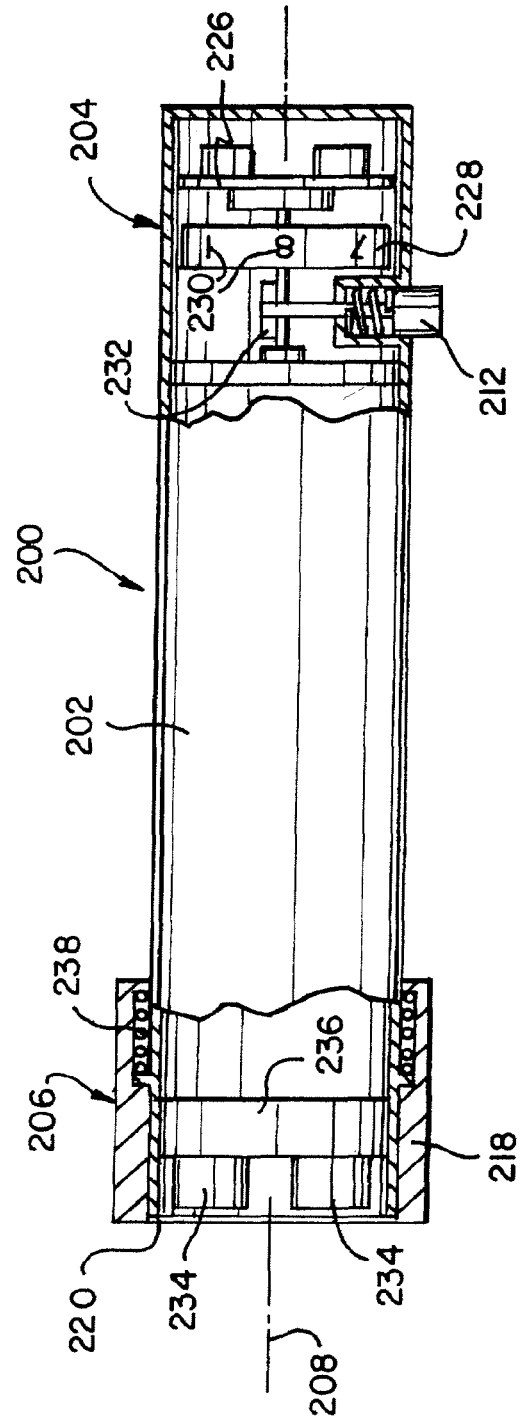

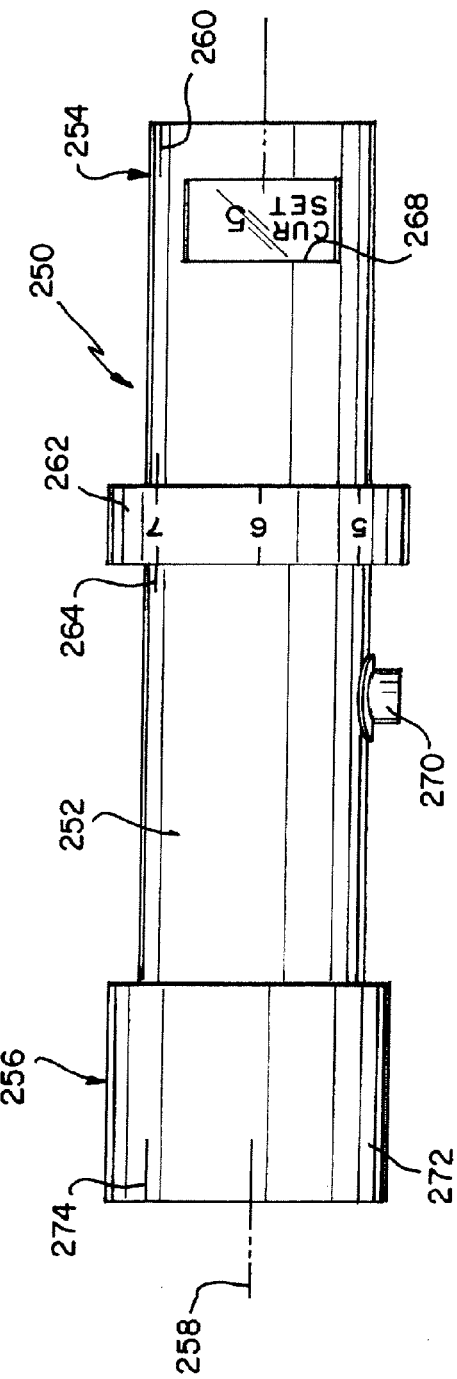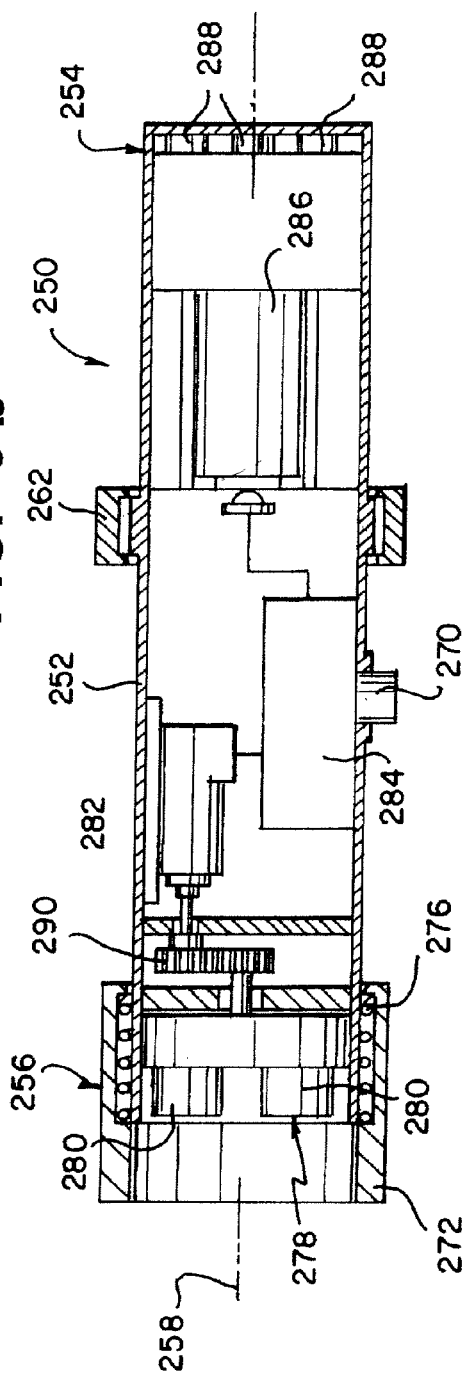

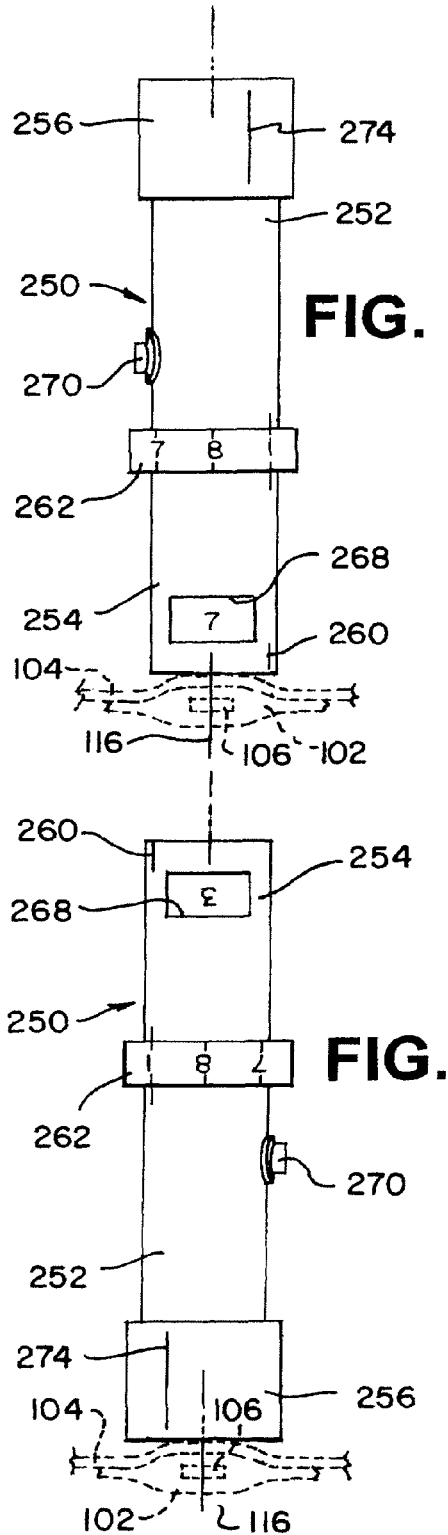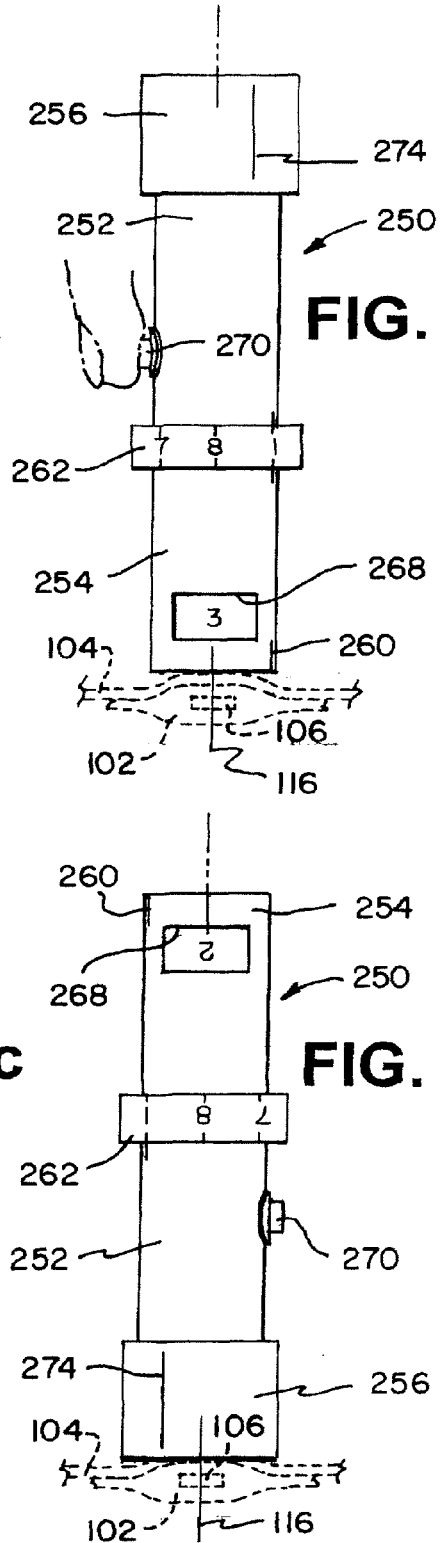

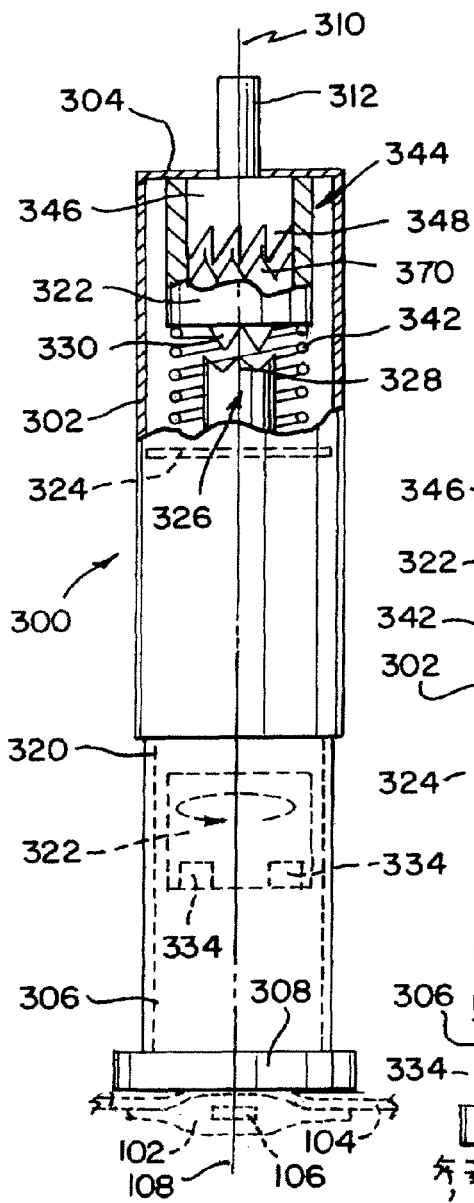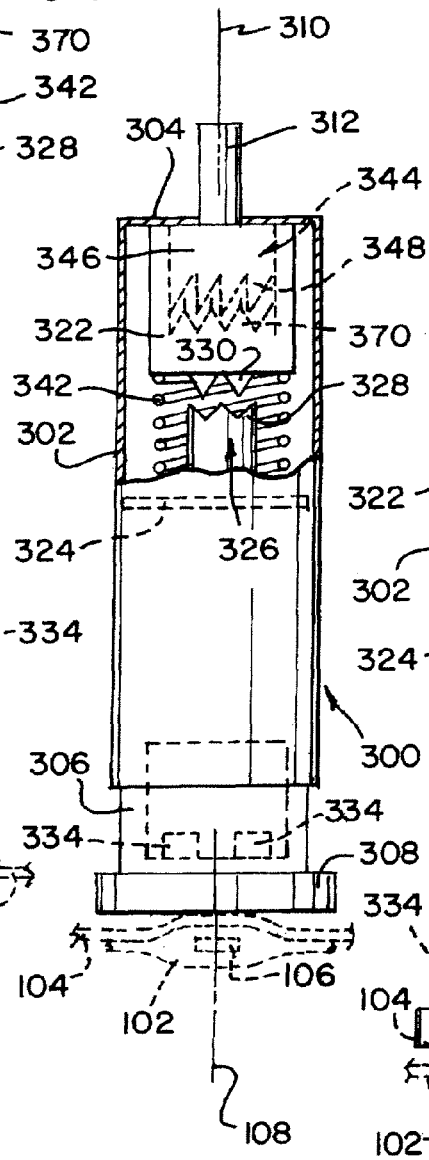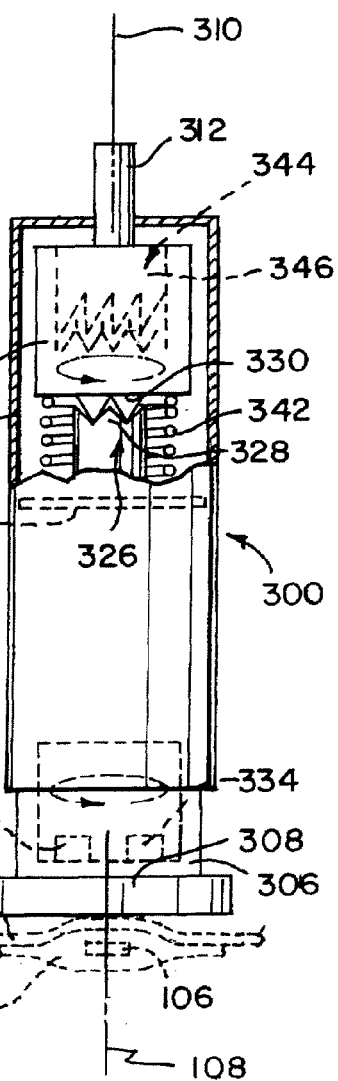

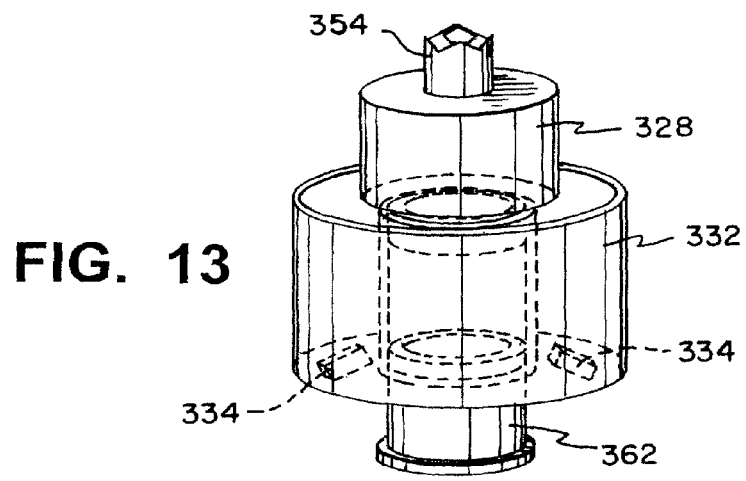
FIG. 13
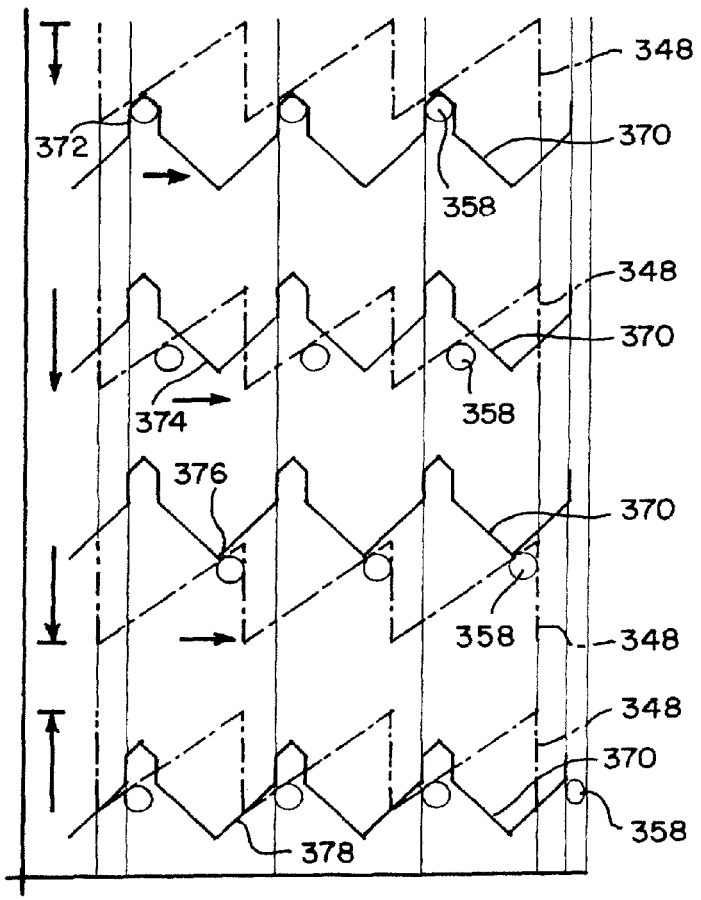
FIG. 14 a
FIG. 14 b
FIG. 14 c
FIG. 14 d

TOOLS AND METHODS FOR PROGRAMMING AN IMPLANTABLE VALVE

FIELD OF THE INVENTION

The invention relates generally to surgically implantable fluid drainage systems. More specifically, the invention relates to extracorporeal tools for reading and setting adjustable valves used for cerebrospinal fluid drainage.

BACKGROUND OF THE INVENTION

Hydrocephalus is a neurological condition caused by the abnormal accumulation of cerebrospinal fluid (CSF) within the ventricles, or cavities, of the brain. Hydrocephalus, which can affect infants, children and adults, arises when the normal drainage of CSF in the brain is blocked in some way. Such blockage can be caused by a number of factors, including, for example, genetic predisposition, intraventricular or intracranial hemorrhage, infections such as meningitis, or head trauma. Blockage of the flow of CSF consequently creates an imbalance between the rate at which CSF is produced by the ventricular system and the rate at which CSF is absorbed into the bloodstream. This imbalance increases pressure on the brain and causes the ventricles to enlarge. Left untreated, hydrocephalus can result in serious medical conditions, including subdural hematoma, compression of the brain tissue, and impaired blood flow.

Hydrocephalus is most often treated by surgically inserting a shunt system to divert the flow of CSF from the ventricle to another area of the body, such as the right atrium, the peritoneum, or other locations in the body where CSF can be absorbed as part of the circulatory system. Various shunt systems have been developed for the treatment of hydrocephalus. Typically, shunt systems include a ventricular catheter, a shunt valve and a drainage catheter. At one end of the shunt system, the ventricular catheter can have a first end that is inserted through a hole in the skull of a patient, such that the first end resides within the ventricle of a patient, and a second end of the ventricular catheter that is typically coupled to the inlet portion of the shunt valve. The first end of the ventricular catheter can contain multiple holes or pores to allow CSF to enter the shunt system. At the other end of the shunt system, the drainage catheter has a first end that is attached to the outlet portion of the shunt valve and a second end that is configured to allow CSF to exit the shunt system for reabsorption into the bloodstream or inside the peritoneum. In some shunt systems, the shunt valve is palpatable by the physician through the patient's skin after implantation.

Shunt valves, which can have a variety of configurations, can be designed to allow adjustment of their fluid drainage characteristics after implantation. It is generally preferred to enable external adjustment of these characteristics to avoid invasive surgical procedures each time an adjustment is required.

In some shunt systems, the shunt valve contains a magnetized rotor to control the pressure threshold of the valve. Physicians can then use an externally applied adjustment mechanism, such as magnetic programmer, to provide a magnetic field to adjust the pressure threshold of the shunt valve. One issue with magnetically programmable valves is a potential for unintentionally adjusting the valve by the misapplication of an external magnetic field. Unintentional adjustment of the valve could lead to either the overdrainage or underdrainage of CSF, which can result in dangerous conditions, such as subdural hematoma. For example, the direction of physical approach to the valve by a magnetic programmer that includes a powerful permanent magnet, or an inappropriate initial rotational orientation of a magnetic programmer with respect to the valve, has the potential to inadvertently change a setting of the valve.

It is also important to be able to externally read or verify the setting of the valve. With some adjustable valves, x-ray images are used to determine the current setting of the valve, before and after adjustment. With other adjustable valves, the orientation of the rotor in the valve can be read magnetically, using a magnetic compass-like device positioned above the valve, outside the skin of the patient.

Although tools and methods exist for adjusting CSF shunt valve settings, as do other tools and methods for reading a valve setting, a need exists for magnetically programmable valve systems having reduced probability of unintentional adjustment, as well as for tools and methods that provide both adjustment and verification of implantable valve settings.

SUMMARY OF THE INVENTION

Accordingly, the present invention provides embodiments of unified tools and methods for externally reading and changing a setting of a magnetically adjustable, implantable valve. In various embodiments, the valve has an external cross section and an internal magnetic rotor. The rotor has a rotor axis about which the rotor can be turned by an externally applied magnetic field to adjust the valve. In some valves, the applied magnetic field also releases a locking device on the rotor, the lock functioning as a safety feature to prevent accidental adjustment of the valve.

One aspect of the present invention is the integration of valve reading and adjusting functions into a single tool, or into a base that can be placed on the patient to read the valve, followed by placement of a magnet on the base to adjust the valve. Another aspect of various embodiments of the invention is a tool having a biased recess for positioning the tool on or above the patient's skin above the implanted valve. The biased recess has an internal cross-section matingly complementary to the external cross section of the valve, so that the tool can be readily positioned on the patient in a specific location relative to the valve and in a unique rotational orientation about a rotational axis of the tool, to help ensure accurate reading and safe adjustments for the patient. Thus positioning the tool using the biased recess also provides alignment of the rotor axis with the tool axis. In other embodiments, the biased recess is not present on the tool, but other orientation markings are provided to assist the user in locating the tool above the valve.

The magnet used to adjust the valve can be a permanent magnet or an electromagnet, rotatable about the axis to perform the adjustment. Embodiments including electromagnets to adjust the valve require that the electromagnet be energized to perform a valve adjustment and are turned off when not in use, while embodiments including permanent magnets for adjusting the valve also incorporate either a magnetic shield or a means for moving the magnet far enough from the valve between adjustments to prevent the occurrence of an accidental adjustment. In some embodiments, a permanent magnet is biased away from the valve by a spring, so that the tool must be pushed toward the valve to bring the magnet close enough to perform a valve adjustment.

Yet another aspect of embodiments of the present invention is a tool that includes a magnetic guide to magnetically couple an adjusting magnet or a magnetic field sensing device, more closely to the rotor. The magnetic guide enables relatively weak magnets to be used for adjusting the valve, and enhances the sensitivity and accuracy of reading the valve. In some embodiments, a rotatable knob is provided for rotating the magnet to adjust the valve, while in others, the adjustment is performed using a pushbutton that provides an incremental rotation of the adjusting magnet each time the pushbutton is pressed. The magnet can also be rotated by a motor or other powered rotary device.

Still another aspect of the present invention is the combination of an adjusting magnet and a device for reading the valve in a single tool. In various embodiments, the reading device is a magnetic compass or an electronically enabled magnetic sensor, such as a Hall effect sensor. Electronically enabled embodiments can include electronic readouts of any kind to report the current setting of the valve or to guide an adjustment. Electronically enabled embodiments can include any type of electrical power source including batteries and capacitors, which can be replaced or recharged by known methods.

Still another aspect of the present invention include an elongated tool having one end for reading the valve and the other for adjusting the valve. Another embodiment employs a single magnet to both read and adjust the valve by having a position close to the valve for the adjustment, and recessed position in which the magnet is free to rotate, performing as a compass. Embodiments of the invention are generally cylindrical in cross section, but any shape that supports the rotational adjustment of the valve can be used.

A further aspect of the present invention is a method for reading and adjusting a magnetically readable valve from a current setting to a target setting, using an integrated tool of the present invention. An embodiment of the method includes positioning the tool, configured for reading, in proximity to the valve and aligned with the rotor. Generally, the tool is placed on or close above the skin of the patient. The current setting of the valve is read, and the tool is switched to an adjusting mode, where a magnetic field from a permanent magnet or an electromagnet is applied to the rotor. The magnet is then rotated and the rotor tracks the rotation of the magnet, to adjust the valve.

DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIGS. 4a and 4b schematically illustrate cross-sectional views of an exemplary, mechanically implemented embodiment of the dual ended tool of FIGS. 3a-3f.

FIGS. 6a and 6b schematically illustrate, respectively, exterior and cross-sectional views of an exemplary, electronically implemented embodiment of a dual-ended integrated tool of the present invention.

FIGS. 7a-7d schematically illustrate an exemplary embodiment of a method for reading and adjusting a magnetically adjustable valve using the dual-ended tool of FIGS. 6a and 6b.

FIGS. 9a-9c schematically illustrate a cross sectional, functional block view of the tool of FIGS. 8a and 8b, and an exemplary method for reading and adjusting a magnetically adjustable valve.

FIGS. 12 and 13 illustrate partial assemblies of the components illustrated in FIG. 11.

FIGS. 14a-14d illustrate details of an incremental rotational adjustment step using tools of the type illustrated in FIGS. 8a-13.

DETAILED DESCRIPTION

Figure 1A:
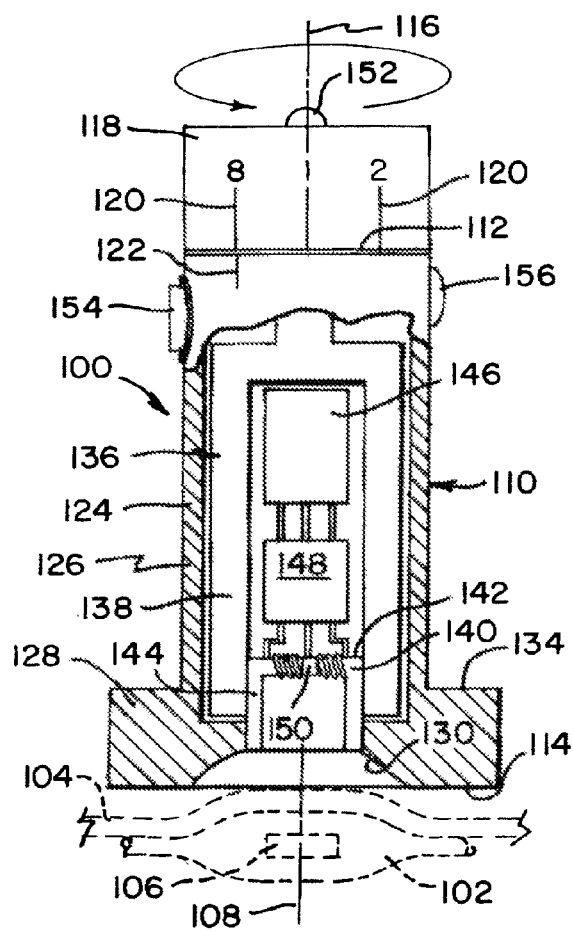
FIG. 1a schematically illustrates a cross sectional view of an exemplary embodiment of an electronically enabled integrated tool of the present invention for reading and adjusting an implantable valve.

Methods and integrated tools of the present invention enable a physician to consistently and reliably read and change a setting of (adjust) an implantable, magnetically settable valve (valve) from a current setting to a target setting using integrated adjustment and reading tools. In an exemplary embodiment, the valve is used to control, via its setting, at least one of CSF drainage flow and pressure for a patient with hydrocephalus, is implanted under a patient's scalp or another portion of the patient's skin, and is adjustable from outside (above) the patient's skin.

Other tools and methods for extracorporeally reading and adjusting a hydrocephalus valve are disclosed in copending U.S. patent application Ser. No. 12/415,590 entitled "Tools and Methods for Programming an Implantable Valve", which is hereby incorporated by reference in its entirety. Within the scope of the present invention, features of the various embodiments disclosed herein can be used in any combination to construct additional integrated tools and methods for reading and adjusting an implantable valve.

Hydrocephalus valves read and adjusted by tools and methods of the present invention comprise a magnetic rotor, the rotational orientation of which about a rotor axis is indicative of, and used to modify, the current setting of the valve. An externally applied magnetic field can be used to rotate the rotor about the rotor axis to adjust the valve to the target setting. Additionally, some hydrocephalus valves include a locking element to prevent accidental adjusting of the valve by stray magnetic fields, requiring that a magnetic field for adjusting the valve be applied along the rotor axis to unlock the valve before turning the rotor about the rotor axis.

Any noninvasive means for applying a magnetic field for adjusting the valve, or for sensing the orientation of the rotor to read the valve, can be incorporated in tools and methods of the present invention. In some embodiments, the externally applied magnetic field for adjusting the valve is provided using one or more permanent magnet that can be physically oriented about the rotor axis. In other embodiments, the externally applied magnetic field for adjusting the valve is provided using one or more electromagnet having a magnetic field that can be electronically or physically oriented about the rotor axis.

Reading the current valve setting is accomplished by sensing the rotational orientation of the magnetic rotor about the rotor axis. In some embodiments, sensing the rotational orientation is accomplished using a magnetically responsive mechanical device such as a magnetic compass. In other embodiments, sensing the rotational orientation is accomplished using one or more Hall effect sensor, which is a solid state electronic device capable of measuring a magnetic field.

In yet other embodiments, sensing the rotational orientation is accomplished using electromagnetic communication with devices such as radio frequency identification (RFID) microelectronic devices that can be incorporated into the valve and respond to an externally applied radio frequency (RF) signal to report one or both of their location and orientation. Some embodiments including electronic components, further include an electronic display on which the current valve setting, notification of completion of a valve adjustment, or another aspect of tool status can be shown. Further, various embodiments include ferromagnetic components for one or both of shielding sensitive components from a magnetic field, and guiding a magnetic field to a desired location.

Referring more particularly to the figures, FIG. 1a schematically illustrates in a cross sectional view, an embodiment of an electronically enabled integrated tool 100 of the present invention, for both reading and adjusting a magnetically adjustable valve 102 implanted beneath a patient's skin 104. The valve 102 includes a magnetic rotor 106 having a rotor axis 108 about which the rotor 106 can be rotated by application of a magnetic field, to adjust the valve 102. In an embodiment, the valve 102 has a plurality of predetermined settings corresponding to a plurality of predetermined rotational orientations of the rotor 106 about the rotor axis 108. In an embodiment, the plurality of settings comprises eight settings.

It is to be understood that the valve 102 can be any magnetically settable, implantable valve comprising a magnetically rotatable rotor, and further including valves that can be magnetically unlocked. In an embodiment, the valve 102 is unlocked for rotation about the rotor axis 108 by a displacement of the rotor along the rotor axis 108, the displacement provided by application an attractive magnetic field along the rotor axis 108. In a further embodiment, the attractive magnetic field and the magnetic field for rotating the rotor about the rotor axis are provided by a single magnetic source that can be either a permanent magnet or an electromagnet.

The integrated tool 100 is seen to comprise a substantially cylindrical outer shell 110 having an upper end 112, a lower end 114, and a longitudinal tool axis 116 extending therebetween. It should be noted that for this and for various other exemplary embodiments of tools disclosed herein, the term "substantially cylindrical" is used illustratively and intended to include any external cross section, for example, another geometrical cross section, that does not comprise features that interfere functionally with the tool.

A knob 118 is seen to extend longitudinally from the upper end 112 of the shell 110. The knob 118 is rotatable about the tool axis 116 with respect to the shell 110, and is seen to comprise a plurality of rotational position markings 120 referenced to a reference mark 122 on an outer surface 124 of the shell 110. In an alternative embodiment, the reference mark is on a surface of the knob 118 and the plurality of rotational position markings is on a surface of the shell 110.

Figure 1B:
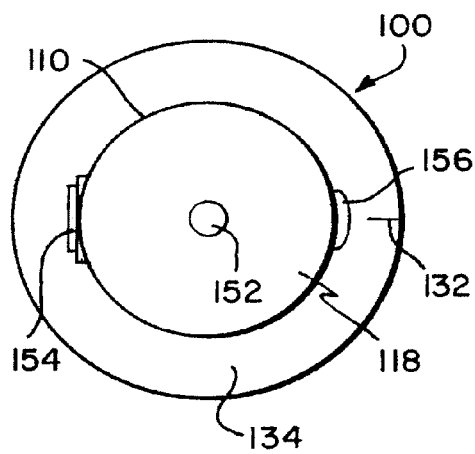
FIG. 1b and FIG. 1c are top and bottom views, respectively, of the embodiment illustrated in FIG. 1a FIGS. 2a-2d illustrate an exemplary embodiment of a valve adjustment method of the present invention using the integrated tool of FIGS. 1a-1c.
Figure 1C:
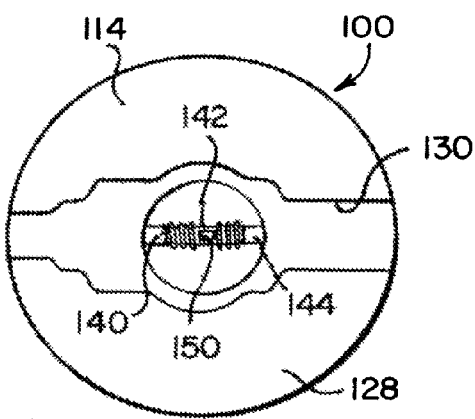

In an embodiment, the knob 118 comprises eight rotational position markings 120, corresponding to eight available settings of the valve 102. The shell 110 is seen to comprise a substantially tubular central portion 126 about the tool axis 116, and a lower portion 128 that includes a biased recess 130. FIG. 1b and FIG. 1c schematically illustrate external top 132 and bottom 134 views, respectively, of the integrated tool 100.

The biased recess 130 is adapted to be matingly complementary in shape to the valve 102, preferably as palpatable through the patient's skin 104. We use the term "biased" herein to mean that the biased recess 130 has a noncircular cross section that can be positioned matingly on the skin 104 above the implanted valve 102, only in a predetermined position on the skin 104 and in a unique rotational orientation of the shell 110 about the tool axis 116. Thus positioning the shell 110 above the valve 102, aligns the tool axis 116 with the rotor axis 108. In an embodiment, the palpatable shape closely corresponds to a manufactured shape of the valve 102, which can be any of a variety of shapes, depending on the specific design and function of the valve 102.

In another embodiment, the rotational orientation of the shell 110 about the tool axis 116 is indicated by one or more orientation marking 132 on an outer surface 134 of the lower portion 128 of the shell 110. In a further embodiment (not illustrated), the biased recess 130 is not present on the shell 110 and the one or more orientation marking 132 provides primary guidance for orienting the shell 110 on the patient's skin 104.

The knob 118 is seen to be mechanically connected to a reading and adjustment assembly 136 rotatably positioned within the shell 110, so that when the knob 118 is rotated about the tool axis 116 with respect to the shell 110, the entire reading and adjustment assembly 136 rotates along with it via a mechanical linkage 138. The reading and adjustment assembly 136 comprises an electromagnet 140 having a core 142, a magnetic guide 144 extending from the core 142 toward the lower end 114, and an electrical power source 146 that can supply electrical power to the electromagnet 140 via an electronic control unit 148. In an embodiment, the power source 146 is an electric battery. In an embodiment, the magnetic guide 144 comprises a ferromagnetic material. In another embodiment, the power source 146 is an ultracapacitor. In yet another embodiment, the power source 146 is inductively rechargeable by a charger (not illustrated) external to the integrated tool 100, using known methods for inductive charging.

The reading and adjustment assembly 136 further comprises one or more Hall effect sensor 150 mounted in proximity to the electromagnet 140. In another embodiment, the reading and adjustment assembly 136 comprises one or more of another type of magnetic sensor. The one or more Hall effect sensor 150 is coupled via the electronic control unit 148 to an electrically powered indicator 152 positioned on an external surface of the integrated tool 100. In various embodiments, the indicator 152 is a light emitter or a sound emitter when electrically energized. In an embodiment, the indicator 152 is a light-emitting diode positioned on the knob 118. In another embodiment, the one or more Hall effect sensor is mounted to the magnetic guide 144.

Electrically connected to the reading and adjustment assembly 136 is a power switch 154 for powering the electronic control unit on and off, and an energizing switch 156 for powering the electromagnet 140 on and off. In an embodiment, one or both of the switches 154, 156 is mounted to the shell 110. In another embodiment, one or both of the switches is mounted to the knob 118. In an embodiment, the energizing switch 156 is a momentary contact switch that, when released, turns off the electromagnet 140.

With the integrated tool 100 positioned over the valve 102, the power switch 154 turned on, and the energizing switch 156 turned off, the one or more Hall effect sensor 150 and an associated portion of the control unit 148 are operational to sense the magnetic field of the rotor 106 via the magnetic guide 144, which enhances the magnetic coupling between the rotor 106 and the one or more Hall effect sensor 150. The sensed magnetic field is dependent on the rotational orientation of the knob 118 via the corresponding orientation of the reading and adjustment assembly 136.

An exemplary embodiment of a method for using the integrated tool 100 to read and adjust the magnetic valve 102 is schematically illustrated in FIGS. 2a-2d. For illustrative purposes in FIGS. 2a-2d, the reference mark 122 is shown in a differently rotated position on the shell 110 than is shown in FIGS. 1a-1c. In the illustrated embodiment, the indicator 152 is a light-emitting diode. FIGS. 2a-2d are external views, with internal components of the integrated tool 100 not shown.

Figure 2A:
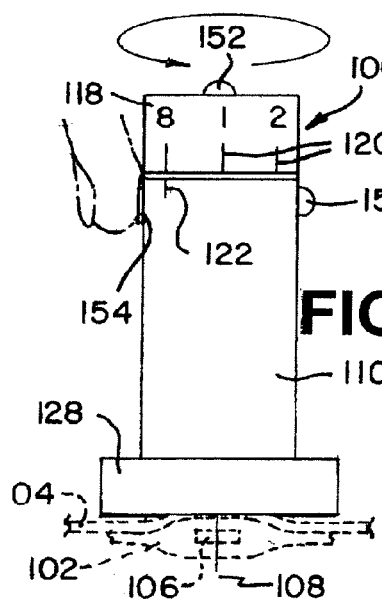
Figure 2B:
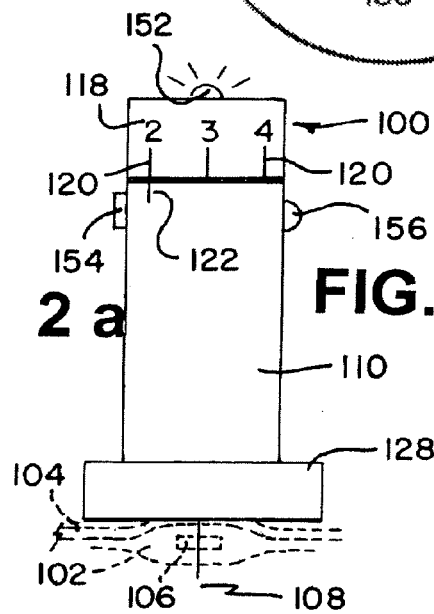
Figure 2:
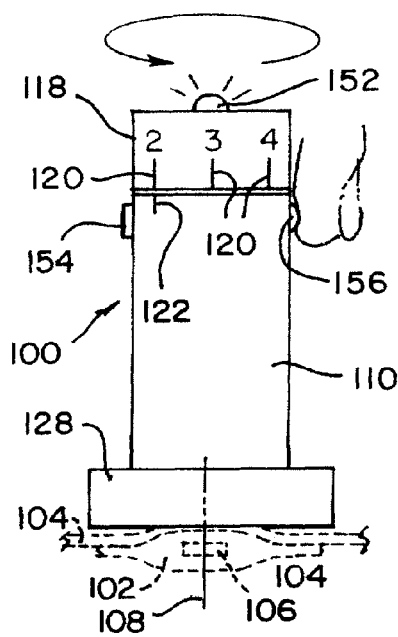
Figure 2:
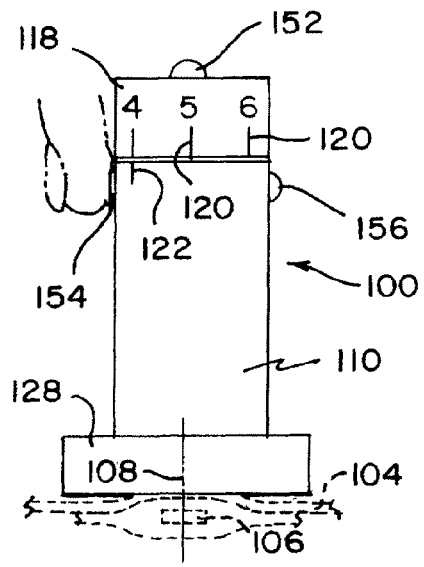

As illustrated in FIG. 2a, the integrated tool 100, positioned matingly over the valve 102, is turned on using the power switch 154. Then the knob 118 is rotated until the orientation of the rotor 106 is sensed by the one or more Hall effect sensor 150, at which rotation, shown as position "2" aligned with the reference mark 122 in FIG. 2b, the indicator 152 is illuminated to report the current valve setting to the user. Turning now to FIG. 2c, the energizing switch 156 is then activated and held to unlock the rotor 106. The knob 118 is then rotated to the target setting, the rotor 106 tracking the rotation of the electromagnet 140.

The magnetic guide 144 provides enhanced coupling between the fields of the electromagnet 140 and the rotor 106, to minimize the power required for the electromagnet to unlock and rotate the rotor 106. In one embodiment, the indicator 152 remains active while the electromagnet 140 is energized. In another embodiment, activation of the electromagnet 140 is displayed to the user as a change in the output of the indicator 152. Once the target setting has been attained, illustrated in FIG. 2d as position "4", the energizing switch 156 is released to turn off the electromagnet 140 and the power switch 154 is turned off to complete the adjustment procedure. In an embodiment, the power switch 154 is automatically turned off by the control unit 148 after a predetermined period of disuse, to conserve energy stored by the electrical power source 146.

The electronically enabled integrated tool 100 has several advantages. As a unitary tool, there are no separable components that could become misplaced or accidently separated from the tool. In addition, reading and adjusting the implanted valve are accomplished without moving the tool with respect to the patient once it is positioned over the valve, thereby improving patient comfort and reducing the probability of operator error relative to the use or multiple tools or repositioning a tool during the procedure. Using an electromagnet that can be turned on and off as needed prevents accidental adjustment of the valve, whereas a powerful permanent magnet used to adjust the valve must be one or both of carefully oriented or magnetically shielded as it approaches the valve, to reduce the likelihood of an accidental adjustment. In addition, coupling the electromagnet to the valve via a magnetic guide minimizes the electric power requirements of the electromagnet. Further, using a single magnetic guide to enhance the magnetic coupling of both the sensor and the electromagnet to the valve rotor provides a basis for the construction of a tightly integrated and highly functional tool.

Also advantageously, using Hall effect sensors or another type of electronic sensor to determine the current valve setting makes the tool completely independent of orientation with respect to the Earth's gravitational field, so it can be used in any orientation. A Hall effect sensor, having no moving parts, is also advantageous relative to the use of magnetic sensing by a weak permanent magnet, such as a relatively physically fragile compass needle, which also has a magnetization that can potentially be changed under influence of a strong magnetic field, such as the magnetic field used to adjust the valve.

Figure 3:
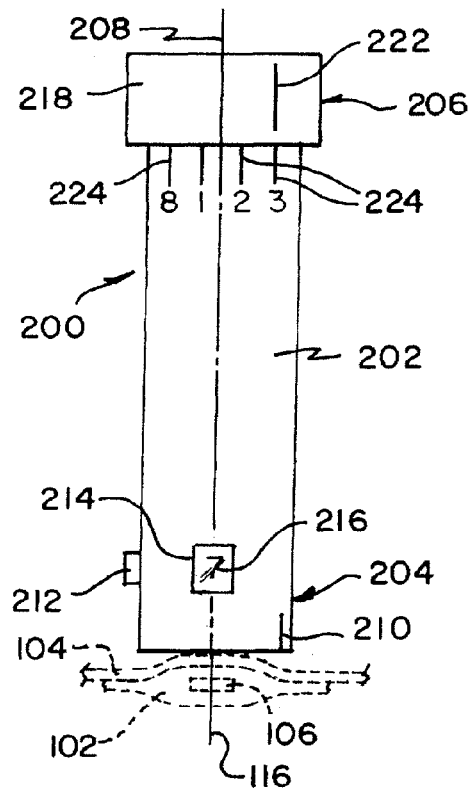
FIGS. 3a-3f schematically illustrate an exemplary embodiment of a dual-ended integrated tool and method of the present invention, for reading and adjusting a magnetically adjustable valve.
Figure 3:
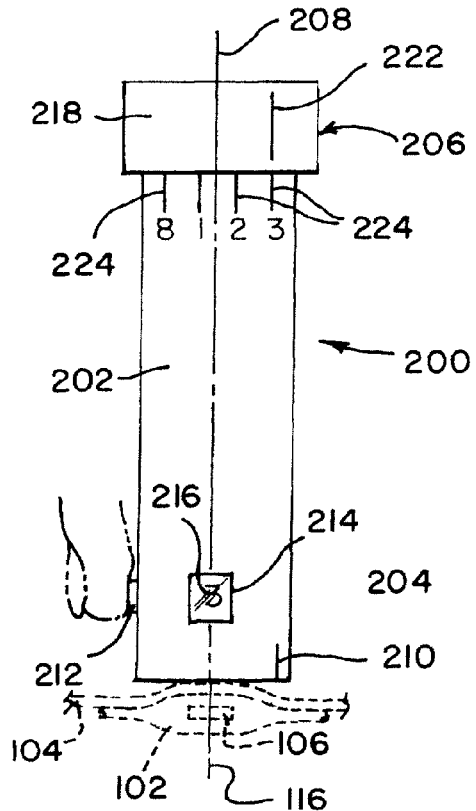
Figure 3C:
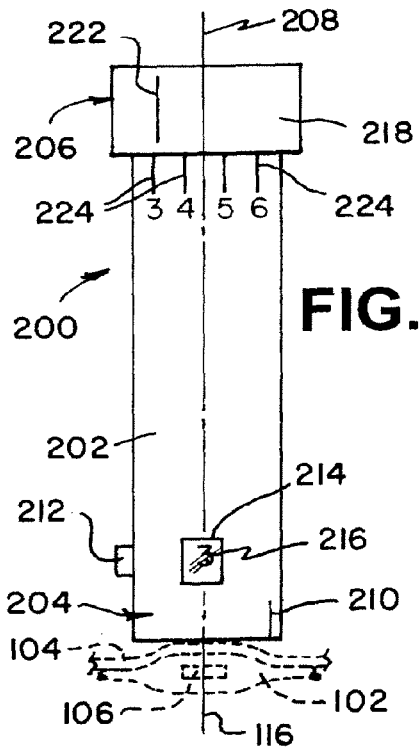
Figure 3D:
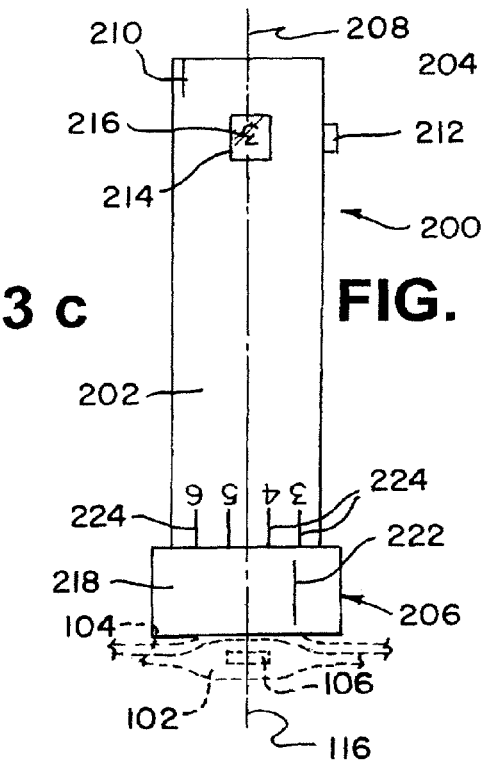
Figure 3E:
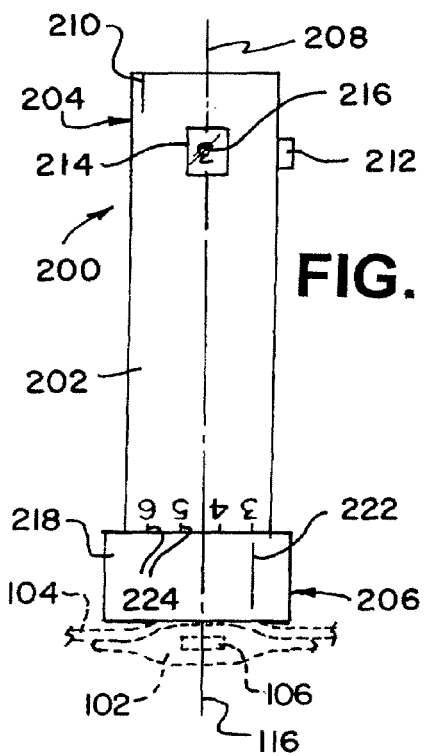
Figure 3F:
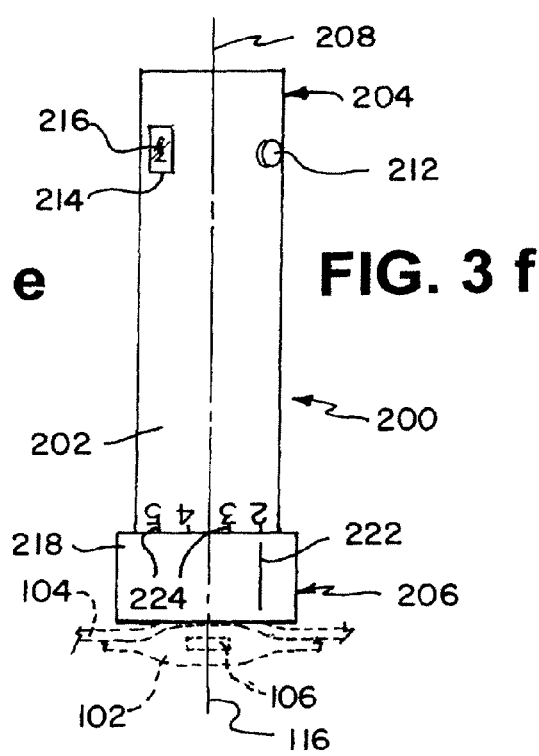

FIGS. 3a-3f schematically illustrate an embodiment of a dual-ended integrated tool 200 and method for reading and adjusting the magnetically adjustable valve 102 implanted beneath the patient's skin 104. Referring to FIG. 3a, the dual-ended tool 200 comprises a substantially cylindrical body 202 having a reading end 204, an adjusting end 206, and a tool axis 208 therebetween. For reading the valve 102, a user of the dual-ended tool 200 aligns the reading end 204 to the valve 102 in a reading orientation, as illustrated in FIGS. 3a-3c. For adjusting the valve 102, the user inverts the dual-ended tool 200 end-over-end to align the adjusting end 206 with the valve 102, as illustrated in FIGS. 3d-3f. In one embodiment, the reading end 204 and the adjusting end 206 are used independently of one another to read and adjust the valve 102, respectively. In another embodiment, reading the current setting of the valve using the reading end 204, programs the adjusting end 206 to the current reading of the valve 102.

Referring to FIGS. 3a-3c, the reading end 204 is seen to comprise one or more read orientation marking 210 for rotationally orienting the dual-ended tool 200 about the tool axis 208 with respect to the valve 102, before reading the valve 102. The reading end 204 is also seen to comprise a read button 212 and a display 214 for displaying the current setting of the valve 102. In one embodiment, the read button 212 is an electrical switch for turning on an electronic circuit within the dual-ended tool 200, thereby activating an array of Hall effect sensors mounted in proximity to the reading end 204. The rotational orientation of the rotor 106 about the rotor axis 116 is read using the Hall effect sensors and reported on the display 214. In an embodiment, the array of Hall effect sensors is a circumferential array, for detecting the orientation of the rotor 106 without having to rotate the dual-ended tool 200 about the tool axis 208. In an embodiment, the number of Hall effect sensors is equal to the number of available valve settings in valve 102. In another embodiment, another type of magnetic field sensor is used to sense the magnetic field of the rotor 106, to read the valve 102.

In yet another embodiment, the read button 212 is a mechanical release that when activated allows a compass-type magnetic field detector mounted within the reading end 204 to freely rotate about the tool axis 208 in response to the magnetic field of the rotor 106. In this embodiment, when the read button 212 is deactivated, the current reading of the valve 102 is retained and continues to be visible in the display 214. In an embodiment, the compass-type detector comprises a plurality of indicator markings 216, only one of which is viewable at a time in the display 214. In an embodiment, the plurality of circumferential markings 216 comprises eight markings, corresponding to eight available settings of the valve 102.

Referring now to FIGS. 3d-3f, the adjusting end 206 is seen to comprise a sleeve 218 about the body 202, the sleeve 218 having a terminating end 220 extending longitudinally beyond the body 202 opposite the reading end 204. The sleeve 218 comprises one or more adjustor orientation marking 222, for rotationally aligning the dual-ended tool 200 above the valve 102, guided by the physical profile of the valve 102 as visible or palpatable through the patient's skin 104. In another embodiment, the terminating end 220 comprises a biased recess having a similar form and function as the biased recess 130 of the integrated tool 100. The surface of the body 202 longitudinally adjacent to the sleeve 218 is seen to comprise a plurality of rotational position markings 224. In an embodiment, the plurality of rotational position markings 224 comprises eight markings, corresponding to eight available settings of the valve 102.

The sleeve 218 is rotatable about the tool axis 208 with respect to the body 202. Alternatively, the body 202 can be rotated about the tool axis 208 within the sleeve 218, to select one plurality of rotational position markings 224, referenced to one of the one or more adjustor orientation marking 222. The sleeve 218 is also axially spring-loaded with respect to the body 202, so that when the dual-ended tool 200 is pressed against the skin 104, as illustrated in FIGS. 3e and 3f, the body 202 slides longitudinally into the sleeve 218, reducing the overall length of the dual-ended tool 200.

Figure 5A:
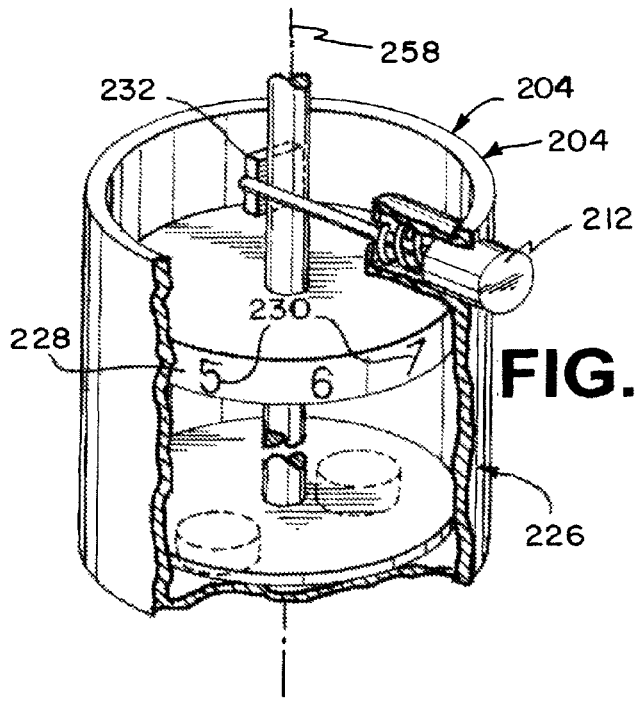
FIGS. 5a and 5b illustrate in cutaway perspective partial views, the reading end of an embodiment of the tool illustrated in FIGS. 4a and 4b.
Figure 5B:
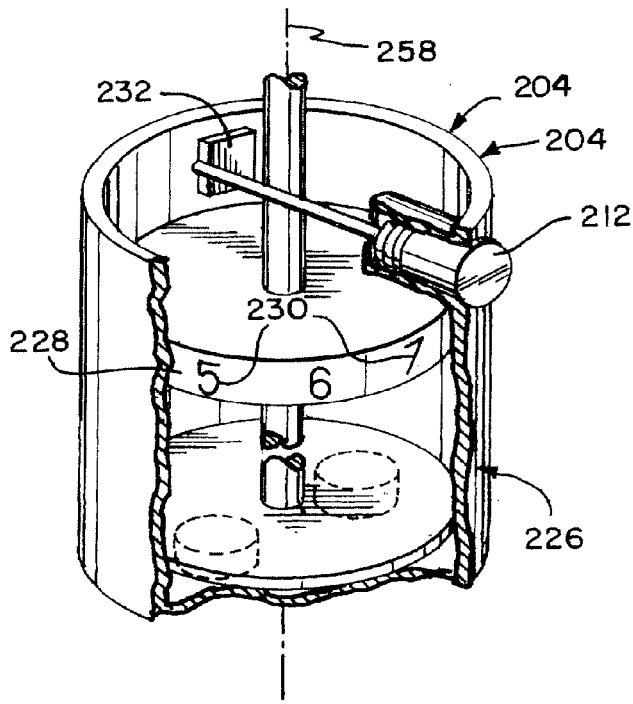

FIGS. 4a and 4b schematically illustrate cross-sectional views of an exemplary, mechanically implemented embodiment of the dual ended tool 200. Referring first to the reading end 204, also illustrated in cutaway perspective partial views in FIGS. 5a and 5b, the double-ended tool 200 is seen to comprise a magnetic compass 226 mechanically coupled to an indicator ring 228 comprising the plurality of circumferential markings 230. In an embodiment, only one of the plurality of markings 230 at a time, corresponding to the current orientation of the compass 226, is visible in the display 214 (as illustrated in FIGS. 3a-3f). With the read button 212 depressed, as illustrated in FIGS. 4a and 5b, the compass 226 is free to rotate about the tool axis 208 in response to an external magnetic field, as when the reading end 204 is brought in proximity to and aligned with the rotor axis 116, as illustrated in FIGS. 3a-3c. With the read button 212 released (deactivated), as illustrated in FIGS. 4b and 5a, a mechanical brake 232 is engaged to prevent the compass 226 from rotating about the tool axis 208.

Now referring to the adjusting end 206 as illustrated in FIGS. 4a and 4b, internally fixed to the body 202 is one or more magnet 234 that, when brought into proximity with the valve 102, is effective to attract the rotor 106 for adjusting the valve 102. As illustrated in FIG. 4a, the one or more magnet 234 is seen to be recessed from the terminating end 220. In an embodiment, a magnetic shield 236 is positioned between the one or more magnet 234 and the compass 226 at the reading end 204, to shield the compass 226 from the magnetic field of the one or more magnet 234. In a further embodiment, the magnetic shield 236 is fabricated from a ferromagnetic material.

The one or more magnet 234 in the recessed position as illustrated in FIG. 4a is distant enough from the terminating end 220 so as not to be effective to adjust the valve 102 when the valve 102 is axially positioned adjacent to or beyond the terminating end 220. The sleeve 218 is seen to comprise a spring 238 that biases the sleeve 218 to extend longitudinally from the body 202 as illustrated in FIG. 4a. An axial force applied to the sleeve 218 at the terminating end 220, for example, by axially pressing the tool against the skin 104 over the valve 102, is effective to slide the sleeve 218 over the body 202 (alternatively stated, to slide the body 202 into the sleeve 218) as illustrated in FIG. 4b, compressing the spring 238 and bringing the one or more magnet 234 closer to the terminating end 220, where it is effective for adjusting the valve 102 when the valve 102 is axially positioned adjacent to the terminating end 220. In an embodiment, the spring 238 is adapted to exert enough axial force to prevent accidental sliding of the sleeve 218 with respect the body 202, but not enough force to cause damage to the patient's skin 104, or significant discomfort. In another embodiment, the sleeve 218 is not present to prevent unintentional adjustment of the valve 102, and instead, a ferromagnetic shield is positioned over the adjusting end to shield the rotor 106 from the one or more magnet 234 until the shield is physically moved or rotated away from between the one or more magnet 234 and the rotor 106.

FIGS. 3a-3f illustrate an embodiment of a method for using the dual-ended tool 200 for reading and adjusting the valve 102. In FIG. 3a, the reading end 204 of the dual-ended tool 200 is seen to be positioned above the valve 102 and, guided by the one or more read orientation marking 210, rotationally aligned with a predetermined feature of the valve 102 as observable through the skin 104. In an embodiment, the predetermined feature is a visible profile of one or more of an inlet of the valve, an outlet of the valve 102, and the valve itself. For a mechanically implemented embodiment of the dual-ended tool 200, the display 214 displays the valve setting from the last time the read button 212 was activated.

Turning to FIG. 3b, the read button 212 is activated for reading the valve 102, and the current setting of the valve 102 is shown in the display 214 (illustrated in FIGS. 3b-3e as setting "2") Once the current setting has been read, the read button 212 is released, and, as illustrated in FIG. 3c, the sleeve 218 is rotated about the tool axis 208 with respect to the body 202, to align the one of the plurality of rotational position markings 224 corresponding the current setting of the valve, to one of the one or more adjustor orientation marking 222. In an embodiment, the dual-ended tool 200 comprises a plurality of circumferential detents between the sleeve 218 and the body 202, to provide positive indications that one of the plurality of rotational position markings 224 is aligned with the one of the one or more adjustor orientation marking 222. Now referring to FIG. 3d, with the adjustor end 206 rotated to the current setting of the valve 102, the dual ended tool 200 is turned end-over-end, to position the adjusting end 206 above the valve 102 and, guided by one or more adjustor orientation marking 222, the body 202 and the sleeve 218 are as a unit rotationally aligned with the predetermined feature of the valve 102, in a similar manner as was done for reading the valve 102.

Now referring to FIG. 3e, the dual-ended tool 200 is axially pressed against the patient's skin 104 over the valve 102 to bring the one or more magnet 234 physically closer to the valve 102 so that the one or more magnet 234 is effective to adjust the valve 102 by magnetically attracting the rotor 106. In an embodiment, the valve 102 is also unlocked for adjustment by the approach of the one or more magnet 234. Finally, turning to FIG. 3f, adjusting the valve 102 is accomplished by rotating the body 202 about the tool axis 208 within the sleeve 218, to align one of the plurality of rotational position markings 224 corresponding a target setting of the valve 102, (illustrated in FIG. 3f as setting "2") to the one of the one or more adjustor orientation marking 222.

FIGS. 6a and 6b schematically illustrate, respectively, exterior and cross-sectional views of an exemplary, electronically implemented embodiment of a dual ended tool 250 of the present invention. The electronically implemented embodiment of the dual ended tool 250 is seen to generally resemble the dual-ended tool 200 disclosed hereinabove, but adapted for use with electronic technology and automation to read and set the valve 102. First referring to FIG. 6a, the electronically implemented dual-ended tool 250 is seen to comprise a substantially cylindrical body 252 having a reading end 254, an adjusting end 256, and a longitudinal tool axis 258 therebetween.

The reading end 254 is seen to comprise one or more read orientation marking 260, analogous in location and function to the read orientation marking 210 associated with the dual-ended tool 200 disclosed hereinabove. Mounted to the body 252 is seen to be a setting ring 262 rotatable about the body 252, for entering a target setting for the valve 102, referenced to a reference marking 264 on the body 252. The body 252 also comprises an electronic display 268 for displaying a current setting of the valve 102, and a start switch 270 to engage a reading and adjustment procedure. In an alternate embodiment, instead of the setting ring 262, another electronic input device is provided that can comprise a thumbwheel, one or more electronic switch mounted to the body 252, or any other electronic input device. In a further embodiment, the electronic display 268 displays the target setting in addition to the current setting of the valve 102.

The adjusting end 256 is seen to comprise a sleeve 272 that is biased to extend longitudinally from an end of the body 252 in the same manner as the sleeve 218 associated with the dual-ended tool 200 disclosed in association with FIGS. 4a and 5a, with the exception that the sleeve 272 illustrated in FIGS. 6a and 6b is not rotatable about the tool axis 258 with respect to the body 252. The sleeve 272 is seen to comprise one or more adjustor orientation marking 274, analogous in location and function to the one or more adjustor orientation marking 222 associated with the dual-ended tool 200 disclosed hereinabove. In an embodiment, the biasing is provided by a compression spring 276 positioned between the body 252 and the sleeve 272. As illustrated in FIG. 6b, internally to the body 252 and rotatably mounted about the tool axis 258 within the body 252 is a magnetic assembly 278 comprising one or more magnet 280 that, when brought into proximity with the valve 102, is effective to attract the rotor 106 for adjusting the valve 102.

In an embodiment, the electronically implemented dual-ended tool 250 also comprises an electric motor 282 effective for rotating the magnetic assembly 278 about the tool axis 258 under control of an electronic control circuit 284 powered by an electrical power source 286 that can be a battery, an ultracapacitor or another power source. In an embodiment, the power source 286 is inductively rechargeable by a charger (not illustrated) external to the electronically implemented dual-ended tool 250. In another embodiment, the magnetic assembly 278 comprises one or more electromagnet that can be energized by the power source 286 via the control circuit 284. The electronic control circuit 284 also controls an array of magnetic sensors 288 that in an embodiment comprises a plurality of Hall effect sensors as disclosed hereinabove for the dual-ended tool 200. In a further embodiment, the motor 282 is coupled to the magnetic assembly 278 through a rotary mechanical linkage 290 that in an embodiment includes rotational speed reduction from the motor 282 to the magnetic assembly 278.

FIGS. 7a through 7d schematically illustrate an exemplary embodiment of a method for using the electronically implemented dual-ended tool 250 to read and adjust the valve 102. FIGS. 7a-7d are external views of the electronically implemented dual-ended tool 250, and internal components thereof are described with reference to FIGS. 6a and 6b. Turning to FIG. 7a, the reading end 254 is aligned to the valve 102 in the same manner as disclosed hereinabove in association with FIG. 3a for aligning the reading end 204 of the dual ended tool 200 with the valve 102. The setting ring 262 is rotated at any time during the procedure to indicate a desired target setting for the valve 102. The setting ring 262 can be set to the target setting at any time during the reading and adjusting procedure.

Now turning to FIG. 7b, the start switch 270 is engaged to read the current setting of the valve 102 using the array of magnetic sensors 288 and to display the current setting on the display 268. In addition, the motor 282 is automatically activated, under control of the electronic control circuit 284, to rotate the magnetic assembly 278 within the body 252 so that the current setting of the valve 102 is aligned with respect to the adjustor orientation marking 274 when the electronically implemented dual-ended tool 250 is turned end-over-end, and the adjusting end is aligned with the valve 102, as illustrated in FIG. 7c, analogous to the procedure disclosed hereinabove in association with FIG. 3d for the dual ended tool 200.

Moving from FIG. 7c to FIG. 7d, analogous the step disclosed hereinabove in association with FIG. 3e for the dual ended tool 200, the electronically implemented dual-ended tool 250 is pressed against the patient's skin 104 to bring the magnetic assembly 278 physically closer to the valve 102 to adjust the valve 102 by magnetically attracting the rotor 106. In an embodiment, when the sleeve 272 is pressed against the skin 104, the motor 282 is automatically engaged to rotate the magnetic assembly 278, to adjust the valve to the target setting, without manually rotating the body 252 about the tool axis 258 within the sleeve 272. In another embodiment, the display 268 updates to show the target setting when the adjustment is complete.

Advantageously, the dual-ended tools disclosed hereinabove are unitary tools having no separable components that could become misplaced or accidently separated from the tool. In addition, the reading and adjusting sections of the tool are physically isolated from one another at opposing ends of the tool and can be magnetically shielded from one another, minimizing any possibility that adjustment magnets can influence a compass reading of the valve. Further, in an embodiment, the valve reading can be retained indefinitely using a compass-type reader, without using any electrical power. In electronically implemented embodiments, the reading and adjustment procedure can be largely automated to further reduce the possibility of an incorrect reading or adjustment, enhancing patient safety and comfort. Also in electronic embodiments, electronic magnetic field sensors such as Hall effect sensors can eliminate interference between valve reading and adjusting functions.

Also advantageously, the dual-ended tool can be made physically small in diameter, providing a small physical profile on the patient's skin, an additional convenience in situations where a valve is implanted in a location that may otherwise be difficult to access for reading and adjusting, such as near a patient's ear. In an embodiment, the dual-ended tool is constructed as a pen-shaped instrument that a medical professional could carry conveniently, for example, in a pocket of a laboratory coat. In a further embodiment, the dual-ended tool comprises a pocket clip, to prevent loss while being transported.

Figure 8A:
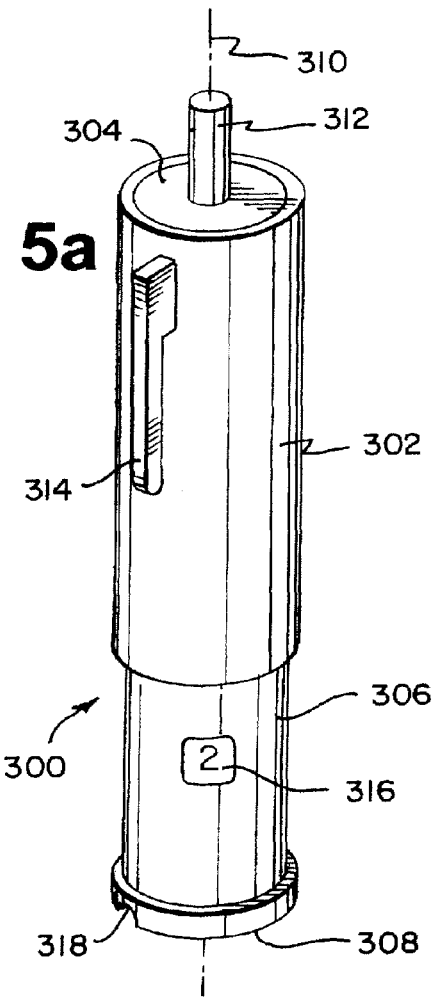
FIGS. 8a and 8b schematically illustrate an exemplary embodiment of a unified function integrated tool of the present invention for reading and adjusting a magnetically adjustable valve, in an external perspective view and in a bottom view, respectively.
Figure 8B:
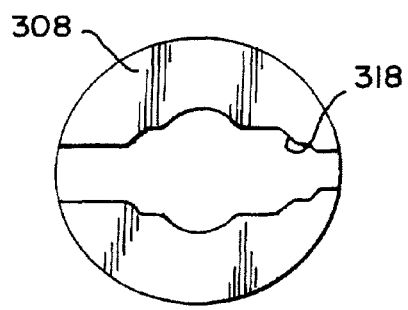

An embodiment of a unified function integrated tool 300 for reading and setting the valve 102 is illustrated in an external perspective view in FIG. 8a and a bottom view in FIG. 8b. The unified function tool 300 is seen to comprise a substantially cylindrical upper section 302 having an upper end 304, a substantially cylindrical lower section 306 having a lower end 308, and a common longitudinal tool axis 310. The upper section 302 and the lower section 306 are slidably coupled to one another along the tool axis 310, with the lower section 306 slidable inside the upper section 302, so that a compressive axial force between the upper 302 and lower section 306 can reversibly slide the lower section 306 further into the upper section 302.

In an embodiment, the compression is against a spring bias internal to the unified function tool 300. In another embodiment, the upper section 302 is slidable within the lower section 306. In an embodiment, sliding the upper 302 and lower 306 section further together switches the unified function tool 300 from a valve reading mode when maximally extended along the tool axis 310, to a valve adjusting mode when maximally compressed along the tool axis 310.

The upper section 302 is seen to comprise a rotational advance button 312 axially extending from the upper end 304. The rotational advance button 312 is adapted to adjust the valve 102 when the unified function tool 300 is in the valve adjusting mode. In an embodiment, the upper section 302 also comprises a clip 314 for releasably securing the unified function tool 300 to a pocket of a garment, or to another object. The lower section 306 is seen to comprise a window 316 for viewing the current setting of the valve 102. In an embodiment, an indication of whether the unified function tool 300 is in the reading mode or the adjusting mode is also viewable in the window 316.

The lower section 306 is also seen to comprise at the lower end 308, a biased recess 318 adapted to be matingly complementary in shape to the valve 102, preferably as palpable through the patient's skin 104. The biased recess 318, analogous in form and function to the biased recess 130 disclosed in association with FIG. 1a for the integrated tool 100, has a noncircular cross section that can be positioned matingly on the skin 104 above the implanted valve 102, only in a predetermined position on the skin 104 and in a unique rotational orientation of the unified function tool 300 about the tool axis 310.

FIGS. 9a-9c schematically illustrate a cross sectional, functional block view of an exemplary embodiment of the unified function tool 300 and an exemplary method for reading and adjusting the valve 102. In FIGS. 9a-9c, the unified function tool 300 is seen to be positioned matingly on the skin 104 above the valve 102, with the tool axis 310 aligned with the valve axis 108. The biased recess 318 is not illustrated in FIG. 9a-9c. Referring first to FIG. 9a, the unified function tool 300 is seen to internally comprise a reading module 320 and an adjusting module 322, mutually separated by an annular disk 324 that is fixed within the upper section 302. The annular disk 324 is seen to comprise a central aperture 326 through which a first rotational locking member 328 extends toward the adjusting module 322. The adjusting module 322 is seen to comprise a second rotational locking member 330, complementary with the first rotational locking member 328. The first 328 and the second rotational locking member 330 are axially engagable with one another to rotationally couple the adjusting module 322 to the reading module 320, as illustrated in FIG. 9c.

Referring to FIG. 9a, the unified function tool 300 is illustrated in the reading mode, maximally extended along the tool axis 310. The reading module 320 is seen to comprise a substantially cylindrical drum 332 that is freely rotatable about the tool axis 310 when in the reading mode. The drum 332 is seen to comprise one or more magnet 334 positioned to rotate the freely rotatable drum 332 about the tool axis 310 under influence of the magnetic field of the rotor 106 in the valve 102, and, in the manner of a magnetic compass, to rotationally align the drum 332 to the rotor 106, thereby reading the current setting of the valve 102. The one or more magnet 334 comprises a magnetic field strong enough to adjust the valve 102 when brought axially in proximity of the valve 102 in the adjusting mode, illustrated in FIGS. 9b and 9c. In the reading mode, as illustrated in FIG. 9a, the drum 332 is spaced apart from the valve 102 along the tool axis 310, the greater distance in the reading mode providing a weaker magnetic interaction between the one or more magnet 334 and the rotor 106, thereby preventing the one or more magnet 334 from unlocking or adjusting the valve 102.

Figure 10:
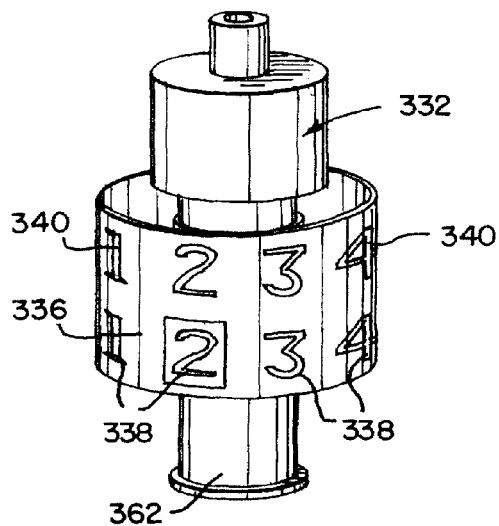
FIG. 10 schematically illustrates an exemplary embodiment of a magnetic drum component of tools of the type illustrated in FIGS. 8-9c.

In an embodiment, as illustrated in FIG. 10, an external surface 336 of the drum 332 comprises a first circumferential plurality of indicators 338 corresponding to the plurality of available settings of the valve 102, one of the plurality of indicators 338 being viewable through the window 316, as illustrated in FIG. 8. In a further embodiment, the drum 332 comprises a second circumferential plurality of indicators 340 corresponding to the plurality of available settings of the valve 102. In an embodiment, the second plurality of indicators 340 is longitudinally displaced from the first plurality of indicators 338 by a distance equal to an axial travel distance of the drum 332 between the reading and adjusting modes, so that in the reading mode, one of the first plurality of indicators 338 is viewable through the window 316, and in the adjusting mode, a corresponding one of the second plurality of indicators 340 is viewable through the window 316. In an embodiment, both the first 338 and the second plurality of indicators 340 comprise numerals, the first 338 and second plurality of indicators 340 being distinguishable from one another by color. In a further embodiment, the first plurality of indicators 338 is black in color, and the second plurality of indicators 340 is red in color.

Upon applying a compressive force to the unified function tool 300, by pressing the upper section 304 toward the valve 102, the unified function tool 300 is switched from the reading mode to the adjusting mode, as illustrated in FIG. 9b. In the adjusting mode, the drum 332 is seen to have been moved closer to the rotor 106 than in the reading mode, for enabling adjustment of the valve 102. In an embodiment, in the adjusting mode, the one or more magnet 334 also unlocks the rotor 106 to enable adjusting the valve 102.

The adjusting module 322 is seen to comprise the advance button 312 that, when pressed axially into the upper section 302, as illustrated in FIG. 9c, axially displaces the second rotational locking member 330 to rotationally lock the adjustment module 322 to the reading module 320. In an embodiment, the adjustment module 322 is biased toward the upper end 304 by a button return spring 342. Further, when the advance button 312 is depressed, a rotational advancement assembly 344 rotates the rotationally locked adjustment module 322 and reading module 320 together as a unit about the tool axis, 310 to adjust the valve 102 incrementally from the current setting to a next adjacent setting of the valve 102.

In an embodiment, the rotational advancement assembly 344 comprises a plurality of stable rotational positions corresponding the plurality of valve settings. In an embodiment, the rotational advancement assembly 344 comprises eight stable rotational positions together comprising 360 degrees of rotation. The rotational advancement assembly 344 can employ any type of incremental rotational advancement that provides rotational steps matching the available valve settings. In an embodiment, the rotational advancement assembly 344 comprises a sawtoothed cylindrical gear 346 having a plurality of teeth 348. In an embodiment, the plurality of teeth comprises eight teeth 348, and each cycle of pressing and releasing the advance button 312 rotates the rotationally locked reading module 320 and adjusting module 322 one eighth of a full rotation (forty-five degrees) about the tool axis 310 with respect to the upper section 302, thereby adjusting the valve 102 one incremental setting. In an embodiment, when the advancement button 312 is pressed, a sloped edge 350 of one or more of the teeth 348 slides against another surface of the rotational advancement assembly 344 to drive the rotation.

Figure 11:
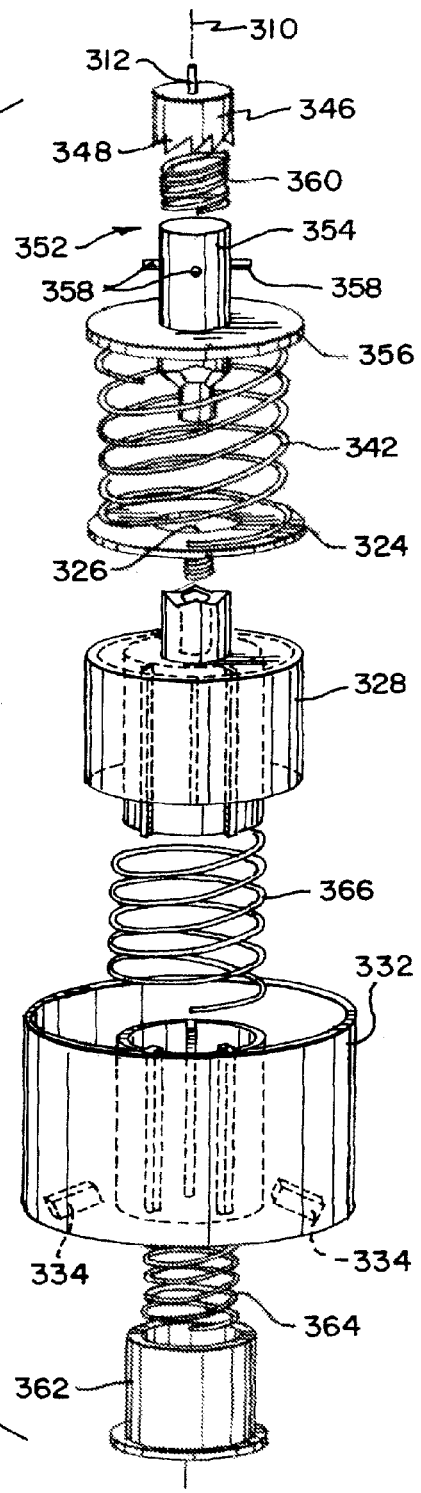
FIG. 11 illustrates an exploded view of internal components of an exemplary embodiment of tools of the type illustrated in FIGS. 8-9c.

FIG. 11 illustrates an exemplary embodiment of components of the reading module 320 and the adjusting module 322, in a collective, exploded view. In this embodiment, adjacent to the advance button 312 and the sawtoothed gear 346 along the tool axis 310, is seen to be a rotation coupler 352 comprising a central cylindrical body 354, a coupler flange 356, and a plurality of transverse pins 358, each adapted to be slidably received between adjacent teeth 348 of the sawtoothed gear 346. The rotation coupler 352 further comprises the second rotational locking member 330 that can engage with the first rotational locking member 238 when the button return spring 342 is compressed and the unified function tool 300 is in the (compressed) adjusting mode. The advance button 312 and the sawtoothed gear are seen to be biased axially apart by a bias spring 360.

The drum 332 is seen to be rotatably and slidably positionable over a bearing base 360 that is fixed to an internal surface of the lower section 306 of the unified function tool 300. The circumferential plurality of indicators 338, 340 are not shown in FIG. 11. The first rotational locking member 328 is seen to be partially slidable into, but rotationally coupled to the drum 332. The drum 332, the bearing base 362, and the first rotational locking member 328 are seen to be biased apart along the tool axis 310. In an embodiment, the drum 332, the bearing base 362, and the first rotational locking member 328 are biased apart by first and second compression springs 364, 366.

Figure 12:
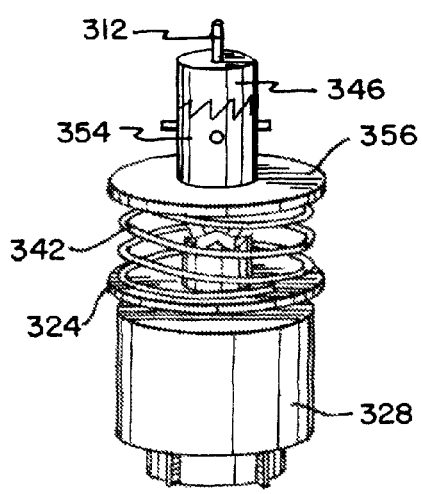

FIGS. 12 and 13 illustrate partial assemblies of the components illustrated in FIG. 11. FIG. 12 illustrates an upper partial assembly, with the advance button 312 and sawtoothed gear 346 mounted to the rotation coupler 352, which is in turn positioned axially adjacent to the first rotational locking member 328. FIG. 13 illustrates a lower partial assembly, showing the first rotational locking member 328 and the bearing base 362 axially engaged with the drum 332 via respective springs 364, 366, providing a freely rotating mounting for the drum 332 between the bearing base 362 and the annular disk 324.

The rotation coupler 352 is rotatable about the tool axis 310 within the upper section 302, while the advance button 312 and the sawtoothed gear 346 are not rotatable. Each of the plurality of pins 358 has an outer end 368 adapted to fit into one of a plurality of shaped receiving notches 370 circumferentially arranged about the interior of the upper section. An incremental rotational adjustment using the rotational advancement assembly 344 is functionally illustrated in FIGS. 14a-14d, where a portion of the plurality of teeth 348 is seen to be coupled to a corresponding portion of the plurality of receiving notches 370 via a corresponding portion of the plurality of pins 358. For illustrative purposes, each of the pluralities of components shown in FIGS. 14a-14d is mapped to a planar, rather than circumferential view, and a horizontal translation in FIGS. 14a-14d corresponds to a rotation in the unified function tool 300.

FIG. 14a illustrates the beginning of a valve adjustment cycle, as the advance button 312 is beginning to be pressed, moving the plurality of teeth 348 downward in FIG. 14a. As the plurality of teeth 368 moves downward, the respective pins 358, and therefore the rotation coupler 252 are pushed downward, at first vertically along a vertical section 372 of the respective notches 370, thereby engaging the first 328 and the second rotational locking member 330 together, rotationally coupling the adjustment module 322 to the reading module 320 for adjusting the valve 102. Now turning to FIG. 14b, as the plurality of teeth 348 continues to move downward, the respective pins 358 travel along a downward sloped portion 374 of the respective notches 370, causing the rotation coupler 252, and therefore the entire rotationally locked reading and adjusting modules, to rotate about the tool axis 310.

At the bottom of travel of the plurality of teeth 348, as illustrated in FIG. 14c, the respective pins 358 have rotationally passed a bottom portion 376 of the respective notches 358, so that as the advance button 312 is released and the plurality of teeth return upward, as illustrated in FIG. 14d, the respective pins 358 travel along an upward sloped portion 378 of a next one of the respective notches 370, causing the rotation coupler 252 to continue rotating about the tool axis 310 until a next vertical portion 380 is reached, wherein the respective pins move vertically, disengaging the first 328 and the second rotational locking member 330 to complete the adjustment cycle. In an embodiment where the plurality of teeth comprises eight teeth, each press and release cycle of the advance button 312 causes a forty-five degree rotation, corresponding to an incremental adjustment of one of eight valve settings.

A method for using the unified function tool 300 to read and adjust the valve 102 is illustrated in FIGS. 9a-9c. FIG. 9a illustrates the unified function tool positioned above and aligned to the valve 102 in the reading mode, wherein the drum 332 is free to rotate about the tool axis 310 to read the valve 102 and display the current setting in the window 316 (shown in FIG. 8a). Now turning to FIG. 9b, the unified function tool 300 is seen to have been axially compressed into the adjusting mode, wherein the drum 332 is now in proximity with the valve, increasing the magnetic coupling between the one or more magnet 334 and the rotor 106, so that the valve can be adjusted. In an embodiment, the valve is unlocked for adjustment as the one or more magnet 334 axially approaches the rotor 106.

Now turning to FIG. 9c, the advance button is seen to have been pressed, rotationally coupling the reading module 320 and the adjusting module 322, and further, rotating the coupled modules to adjust the valve by incrementing the valve setting. Once the valve setting has been incremented, the adjusting step of FIG. 9c can be repeated until a required valve adjustment has been completed, and the tool removed from its position above the valve 102.

The unified function integrated tool 300 has several advantages. As an integrated tool, reading and adjusting an implantable valve can be performed with a single tool. The unified function tool 300 also has its reading mode as a spring-biased default configuration, preventing accidental adjustment of the valve by positioning the adjusting magnet recessed from an end of the tool. Further, the tool can be used to read and adjust the valve without having to move the tool once positioned on the patient, reducing any chance of user error while enhancing patient safety and comfort. Further advantageously, the unified function tool 300 comprises a single magnetic assembly to both read and adjust the valve, thereby eliminating any possibility of interference between a reading magnet and an adjusting magnet.

Figure 15A:
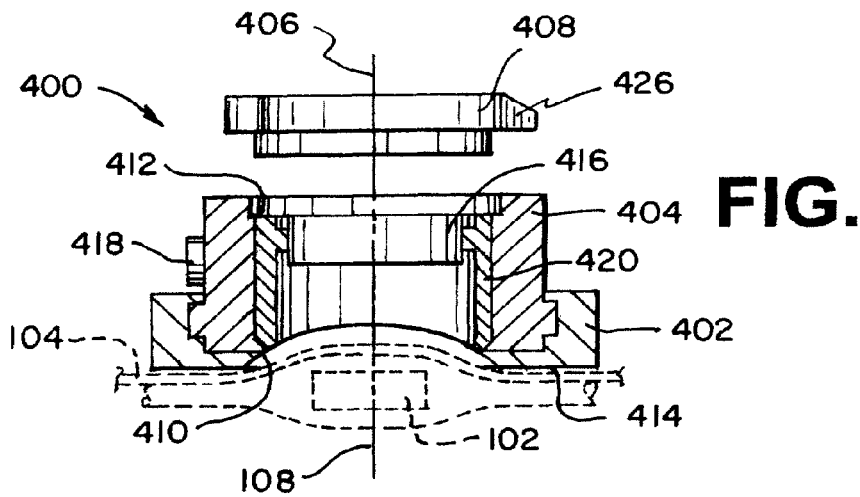
FIGS. 15a and 15b schematically illustrate in cross sectional views, an exemplary embodiment of a two-part tool of the present invention, for reading and adjusting a magnetically adjustable valve.
Figure 15B:
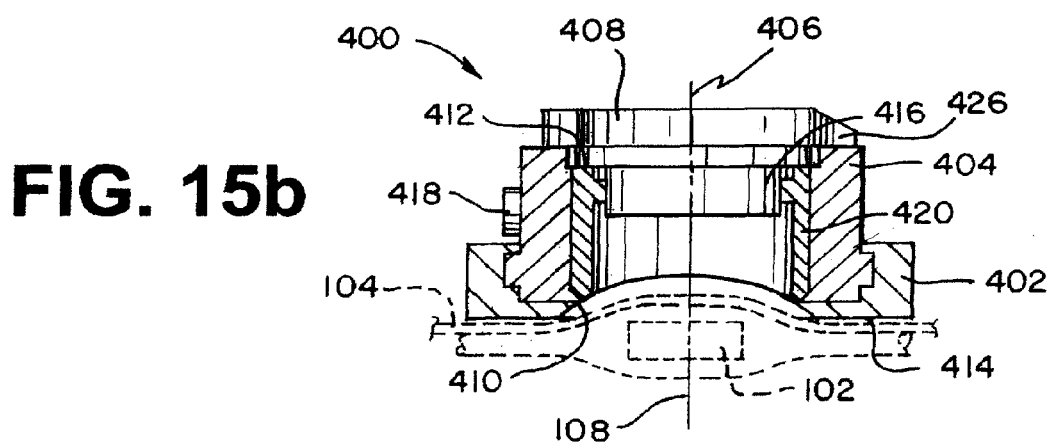

FIGS. 15a and 15b schematically illustrate in cross sectional views, an exemplary embodiment of a two-part tool 400 of the present invention, for reading and adjusting the valve 102. The two-part tool 400 is seen to comprise a base 402, a rotatable core 404 that is rotatable substantially within the base 402 about a tool axis 406, and a separable adjusting magnet 408 releasably mountable to the rotatable core 404. FIG. 15a illustrates the two-part tool 400 in a reading mode, the adjusting magnet 408 being separated from the rotatable core 404, and FIG. 15b illustrates the two-part tool 400 in an adjusting mode, the adjusting magnet 408 being mounted to the rotatable core 404.

The base 402 is seen to comprise a biased recess 410 adapted to be matingly complementary in shape to the valve 102, preferably as palpatable through the patient's skin 104. The biased recess 410, analogous in form and function to the biased recess 130 disclosed in association with FIG. 1a for the integrated tool 100, has a noncircular cross section that can be positioned matingly on the skin 104 above the implanted valve 102, only in a predetermined position on the skin 104 and in a unique rotational orientation of the two-part tool 400 about the tool axis 406.

The rotatable core 404 is seen to have an upper surface 412 and a lower surface 414, the upper surface 412 being adapted to receive and releasably retain the adjusting magnet 408 in a predetermined orientation about the tool axis 406 with respect to the rotatable core 404. The rotatable core 404 is also seen to comprise a magnetic compass 416 for reading the current setting of the valve 102, the compass 416 being readable at the top surface 412. The compass 416 is by default mechanically locked against rotation to read the valve 102, and further comprises a release button 418 that, when mechanically pressed, releases the compass 416 to read the current setting of the valve 102. In another embodiment, one or more magnetic sensor to read the current setting of the valve 102, and the rotatable core 404 further comprises a power source and an electronic display that can be viewed at the upper surface 412.

The rotatable core 404 also comprises one or more magnetic guide 420 that provides magnetic coupling among the upper surface 412, the lower surface 414 and the compass 416. In an embodiment, the one or more magnetic guide 420 comprises a ferromagnetic material. In the reading mode illustrated in FIG. 15a, the one or more magnetic guide 420 magnetically couples the compass 416 to the rotor 106, enhancing the ability of the compass 416 to sense the orientation of the rotor 106 while the release button 418 is depressed, and thereby to read the current valve setting. In the adjusting mode as illustrated in FIG. 15b, the adjusting magnet 408 is seen to be positioned on the upper surface 412, and coupled via the one or more magnetic guide 420 to the rotor 106. While the compass 416 is mechanically locked (release button 418 not pressed), its reading is not influenced by the presence of the adjusting magnet 408.

The presence of the magnetic guide 420 enables a less powerful magnet to be used as the adjusting magnet 408 than would be required without the magnetic guide 420, thereby reducing the risk of an accidental adjustment of the valve 102 as the adjusting magnet 408 is physically moved toward or away from the rotatable core 403 before and after a valve adjustment, respectively.

Figure 16:
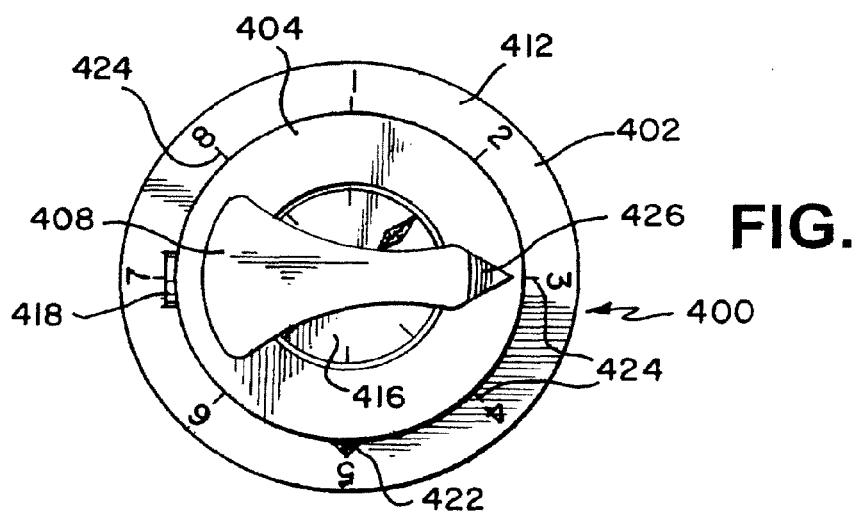
FIG. 16 schematically illustrates a top view of the two-part tool illustrated in FIGS. 15a-15b.

FIG. 16 schematically illustrates a top view of the two-part tool 400 in the adjusting mode, with the adjusting magnet 408 mounted to the rotatable core 404 above and magnetically coupled to the one or more magnetic guide 420. In an embodiment, the adjusting magnet 408 and the upper surface 412 comprise complementary physical features that provide positioning of the adjusting magnet 408 on the upper surface only in a single predetermined location and rotational orientation about the tool axis 406.

The base 402 is seen to comprise one or more tool alignment marking 422 for indicating the orientation in which to position the two-part tool 400 above the valve 102 on the patient's skin 104. The base 402 is seen to further comprise a circumferential plurality of indicator markings 424 corresponding to the plurality of available valve settings. In an embodiment, the plurality of indicator markings 424 comprises eight markings. The rotatable core 414 is seen to comprise a reference marking 426 for indicating one of the plurality of indicator markings 424, selected by the rotational orientation of the rotatable core 404 about the tool axis 406 with respect to the base 402.

In an exemplary procedure for reading and adjusting the valve 102 using the two-part tool 400, with reference to FIGS. 15a-16, the base 412, separated from the alignment magnet 108, is first seen to positioned and aligned on the patient's skin 104 above the valve 102. The release button 418 is then pressed to release the compass 416 to read the current setting of the valve 102. The rotatable core 404 is manually rotated about the tool axis 406 to align the reference marking 426 with the one of the plurality of indicator markings 424 indicated by the compass reading, as the current setting of the valve 102.

Now turning to FIG. 15b, the adjusting magnet 408 is seen to be mounted to the upper surface 412 of the rotatable core 404. In an embodiment, mounting the adjusting magnet 408 to the rotatable core 404 unlocks the valve 102. The rotatable core 404 is then rotated about the tool axis 406 to a target setting of the valve 102. The adjusting magnet 408 is then removed from the rotatable core. In an embodiment, the release button 418 is then pressed again to verify the adjustment, by reading the new setting of the valve 102.

The two-part tool 400 has several advantages. By employing a magnetic guide to couple an adjusting magnet with the valve rotor, a less powerful magnet can be used that would otherwise be required to adjust the valve. Less powerful adjusting magnets reduce the possibility of unintentionally adjusting the valve, and enable the construction of a lighter, more portable reading and adjusting tool. In addition, coupling between the adjusting magnet and the magnetic guide depends very strongly on their separation distance, so the adjusting magnet does not significantly affect the rotor until it is brought in contact with the magnetic guide.

The magnetic guide in the two part tool, by also providing close magnetic coupling between the rotor and the compass, also advantageously reduces the dependence of the compass operation on its orientation with respect to the earth's magnetic field. In some embodiments, sensing the magnetic field of the rotor is done electronically, providing an even more mechanically and magnetically robust tool than already provided by providing a magnetic guide in combination with a compass to read the valve.

Advantageously, embodiments of tools and methods of the present invention provide means to smoothly integrate reading, adjusting, and verifying the setting of an implanted valve in straightforward, repeatable procedures. In addition, embodiments of the present invention enable the reading and adjusting of an implantable valve to a target setting with reduced risk of inadvertently or incorrectly adjusting the valve. The reduced risk of misadjustment enhances patient comfort and safety, as inappropriate adjustment could lead to either the overdrainage or underdrainage of CSF, which can result in dangerous conditions, such as subdural hematoma.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A tool for reading and changing a setting of an implantable valve, the valve having an external cross section and an internal magnetic rotor with an associated magnetic field, the rotor having a rotor axis, the tool comprising:
   a substantially cylindrical body having an upper end, a lower end, a longitudinal axis therebetween, an axial bore along at least a portion of the body between the upper and lower end; a recess at the lower end, the recess having an internal cross-section matingly complementary to the external cross section of the valve, the recess adapted to be positioned in proximity to the valve in a unique rotational orientation about the rotor axis;
   an electromagnet positioned within the bore, a magnetic guide extending from the electromagnet toward the lower end, the magnetic guide adapted to magnetically couple the electromagnet to the rotor, the electromagnet being rotatable about the longitudinal axis; wherein rotating the electromagnet about the axis is effective to adjust the valve by rotating the rotor about the rotor axis.

2. The tool according to claim 1 wherein the electromagnet is mechanically coupled to a rotatable knob at the upper end of the tool, for rotating the electromagnet about the longitudinal axis.

3. The tool of claim 1 further comprising a magnetic field sensor mechanically coupled to one of the electromagnet and the magnetic guide, the magnetic field sensor effective for sensing the rotational orientation of the rotor about the rotor axis.

4. The tool of claim 3 wherein the magnetic field sensor is a Hall effect sensor.

5. The tool of claim 3 further comprising an electronic display for indicating the rotational orientation of the magnetic field sensor relative to the rotor.

6. The tool of claim 1 further comprising an electrical power source positioned within the bore.

7. The tool of claim 6 wherein the electrical power source is one of a battery and a capacitor.

8. A method for reading and changing a current setting of a magnetically readable and settable valve implanted in a patient, the valve having a physical shape and orientation palpatable through the skin of the patient, the method comprising:
   providing a tool comprising an electromagnet, a magnetic field sensor, a magnetic guide for magnetically coupling the electromagnet and the magnetic sensor to the rotor, a recess of the tool adapted to be positioned in a unique orientation above the skin of the patient in proximity to the valve;
   positioning the recess in the unique orientation above the patient's skin in proximity to the valve;
   reading the current setting of the valve by electrically energizing the magnetic sensor;
   and changing the current setting of the valve by electrically energizing the electromagnet and rotating the electromagnet about a common rotational axis between the tool and the rotor.

9. The method of claim 8 wherein reading the current setting of the valve comprises rotating the electromagnet and the magnetic sensor together about the common axis until an electronic signal is generated to indicate that the current setting has been read.

10. The method of claim 9 wherein the electronic signal is converted to at least one of a visual and an acoustic signal.

* * * * *